(12) United States Patent
Tachibana

(10) Patent No.: US 12,133,635 B2
(45) Date of Patent: Nov. 5, 2024

(54) ENDOSCOPE PROCESSOR, TRAINING DEVICE, INFORMATION PROCESSING METHOD, TRAINING METHOD AND PROGRAM

(71) Applicant: HOYA CORPORATION, Tokyo (JP)

(72) Inventor: Toshio Tachibana, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 427 days.

(21) Appl. No.: 17/636,199

(22) PCT Filed: Sep. 20, 2019

(86) PCT No.: PCT/JP2019/036940
§ 371 (c)(1),
(2) Date: Feb. 17, 2022

(87) PCT Pub. No.: WO2021/053808
PCT Pub. Date: Mar. 25, 2021

(65) Prior Publication Data
US 2022/0202284 A1    Jun. 30, 2022

(51) Int. Cl.
*A61B 1/045* (2006.01)
*A61B 1/00* (2006.01)
*A61B 1/273* (2006.01)

(52) U.S. Cl.
CPC ........ *A61B 1/045* (2013.01); *A61B 1/000096* (2022.02); *A61B 1/2736* (2013.01)

(58) Field of Classification Search
None
See application file for complete search history.

(56) References Cited

U.S. PATENT DOCUMENTS

2020/0237184 A1   7/2020  Shigeta
2021/0082568 A1*  3/2021  Kamon ................. G16H 30/40
2021/0166066 A1*  6/2021  Ando .................... G06V 10/764

FOREIGN PATENT DOCUMENTS

JP    2018-139848    9/2018
WO    2019/078237    4/2019

OTHER PUBLICATIONS

Official Communication issued in International Bureau of WIPO Patent Application No. PCT/JP2019/036940, dated Dec. 10, 2019, along with an English translation thereof.

* cited by examiner

*Primary Examiner* — Leon Flores
(74) *Attorney, Agent, or Firm* — GREENBLUM & BERNSTEIN, P.L.C.

(57) ABSTRACT

A processor for an endoscope or the like that assists an endoscopic examination using an appropriate reference image is provided. A processor for an endoscope includes an image acquisition unit that acquires an endoscope image; a region acquisition unit that inputs the endoscope image acquired by the image acquisition unit to a first learning model that outputs a target region corresponding to a predetermined region to be photographed when the endoscope image is input to acquire the target region; and an image output unit that outputs the endoscope image acquired by the image acquisition unit and an index indicating the target region acquired by the region acquisition unit with the endoscope image and the index superimposed.

19 Claims, 35 Drawing Sheets

| PHOTOGRAPHING SEQUENCE | REGION NAME | REFERENCE IMAGE |
|---|---|---|
| 1 | UPPER ESOPHAGUS | ST01.bmp |
| 2 | MIDDLE ESOPHAGUS | ST02.bmp |
| 3 | LOWER ESOPHAGUS | ST03.bmp |
| 4 | ESOPHAGOGASTRIC JUNCTION | ST04.bmp |
| 5 | LOOKING DOWN ON UPPER POSTERIOR WALL OF STOMACH BODY | ST05.bmp |
| 6 | LOOKING DOWN ON MIDDLE POSTERIOR WALL OF STOMACH BODY | ST06.bmp |
| 7 | LOOKING DOWN ON LOWER POSTERIOR WALL OF STOMACH BODY | ST07.bmp |
| 8 | LOOKING DOWN ON UPPER POSTERIOR WALL OF STOMACH CORNER | ST08.bmp |
| 9 | LESSER CURVATURE OF ANTRUM | ST09.bmp |
| 10 | POSTERIOR WALL OF ANTRUM | ST10.bmp |
| 11 | GREATER CURVATURE OF ANTRUM | ST11.bmp |
| 12 | ANTERIOR WALL OF ANTRUM | ST12.bmp |
| 13 | J TURN OF STOMACH CORNER | ST13.bmp |
| ⋮ | ⋮ | ⋮ |

| DOCTOR ID | D123 |
|---|---|
| MEDICAL EXAMINEE ID | ABCDEF |
| DATE | 2019/9/2 |

| NUMBER | REGION NAME | SIMILARITY | IMAGE |
|---|---|---|---|
| 1 | UPPER ESOPHAGUS | 80 | A001.bmp |
| 2 | MIDDLE ESOPHAGUS | 85 | A002.bmp |
| 3 | LOWER ESOPHAGUS | 80 | A003.bmp |
| 4 | ESOPHAGOGASTRIC JUNCTION | 75 | A004.bmp |
| 5 | — | — | A005.bmp |
| 6 | — | — | A006.bmp |
| 7 | LOOKING DOWN ON UPPER POSTERIOR WALL OF STOMACH BODY | 75 | A007.bmp |

FIG. 32

PATIENT ID ABCDEF END

NUMBER OF CAPTURED IMAGES: 35
AVERAGE SIMILARITY: 82 POINTS
HIGHEST SIMILARITY: 95 POINTS
MINIMUM SIMILARITY: 75 POINTS
— 79

FIG. 33

| MEDICAL EXAMINEE ID | ABCDEF |
|---|---|

| PHOTOGRAPHING DATE | IMAGE |
|---|---|
| 2017/8/4 | I170804BMP |
| 2018/8/2 | I180802bmp |
| 2019/8/10 | I190810.bmp |

ENDOSCOPE PROCESSOR, TRAINING DEVICE, INFORMATION PROCESSING METHOD, TRAINING METHOD AND PROGRAM

TECHNICAL FIELD

The present invention relates to a processor for an endoscope, a training device, an information processing method, and a program.

BACKGROUND ART

In an endoscopic examination in a complete medical checkup, a periodic medical examination, or the like, it is necessary not only to discover a lesion but also to observe the entire interior wall of an organ to determine that no lesion is present. In the guidelines set by the medical society, each medical institution, and the like, a region or the like whose image is recorded is set. By recording the image according to the guidelines, it is possible to implement prevention of overlooking of the lesion and double check in which the endoscope specialist doctor confirms the image at a later date.

An endoscope system that assists recording of an image according to the guidelines by determining similarity between an endoscope image being captured and a reference image according to the guidelines has been proposed (Patent Literature 1). In the endoscope system of Patent Literature 1, an examination region being observed is determined based on an insertion length of an insertion portion inserted into a medical examinee, thereby selecting a reference image corresponding to the examination region.

CITATION LIST

Patent Literature

Patent Literature 1: JP 2018-139848 A

SUMMARY OF INVENTION

Technical Problem

However, for example, in the endoscopic examination of the stomach, since the endoscope is variously operated inside the stomach inflated by the air, the insertion length does not correspond to the examination region. Also, in the endoscopic examination of the large intestine, since the intestinal tract is folded in a bellows shape outside the insertion portion, the insertion length does not correspond to the examination region. Therefore, in the endoscope system of Patent Literature 1, it is difficult to select an appropriate reference image and assist the doctor.

In an aspect, an object is to provide a processor for an endoscope or the like that assists an endoscopic examination using an appropriate reference image.

Solution to Problem

A processor for an endoscope includes an image acquisition unit that acquires an endoscope image, a region acquisition unit that inputs the endoscope image acquired by the image acquisition unit to a first learning model that outputs a target region corresponding to a predetermined region to be photographed when the endoscope image is input to acquire the target region, and an image output unit that outputs the endoscope image acquired by the image acquisition unit and an index indicating the target region acquired by the region acquisition unit with the endoscope image and the index superimposed.

Advantageous Effects of Invention

In an aspect, it is possible to provide a processor for an endoscope or the like that assists an endoscopic examination using an appropriate reference image.

BRIEF DESCRIPTION OF DRAWINGS

FIG. 3 is an explanatory diagram for explaining a record layout of a reference image DB.
FIG. 4 is an explanatory diagram for explaining a record layout of an examination DB.

FIG. 32 is an explanatory diagram for explaining a screen display example of a sixth embodiment.

FIG. 33 is an explanatory diagram for explaining a record layout of a follow-up observation DB.

DESCRIPTION OF EMBODIMENTS

First Embodiment

FIG. 1 is an explanatory diagram for explaining an outline of an automatic imaging function. In the present embodiment, a case where an endoscopic examination of the stomach is performed in accordance with the guidelines set by Japanese Society of Gastrointestinal Cancer Screening will be described as an example. The guidelines may be set independently in each medical institution or the like. The organ to be examined may be a large intestine, duodenum, or the like.

Figure 1A:
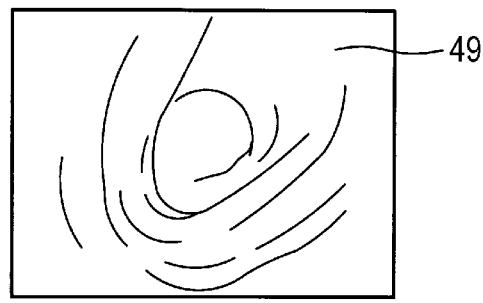
FIG. 1A is an explanatory diagram for explaining an outline of an automatic imaging function.

The doctor inserts an endoscope 30 (see FIG. 2) into the medical examinee who receives the medical examination, and observes an endoscope image 49 in real time. FIG. 1A illustrates a state in which a region to be photographed corresponding to a reference image defined in the guidelines is not included in the endoscope image 49. The doctor appropriately operates the endoscope 30 to direct the visual field to the region to be photographed.

Figure 1B:
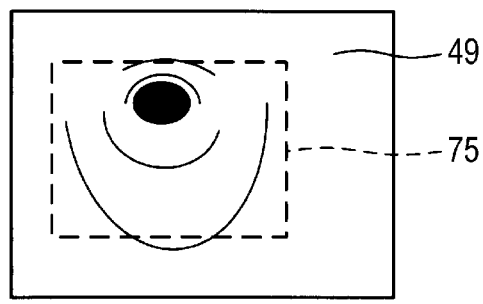
FIG. 1B is an explanatory diagram for explaining an outline of an automatic imaging function.
Figure 1C:
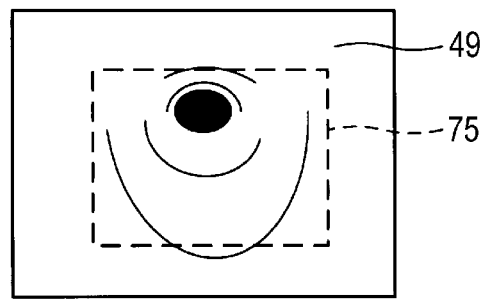
FIG. 1C is an explanatory diagram for explaining an outline of an automatic imaging function.
Figure 1D:
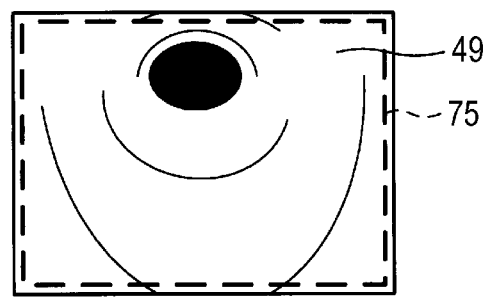
FIG. 1D is an explanatory diagram for explaining an outline of an automatic imaging function.

FIG. 1B illustrates a state in which a region to be photographed is included in the endoscope image 49. A portion corresponding to the reference image is surrounded by the guide frame (bounding box) 75. As illustrated in FIGS. 1C and 1D, the doctor operates the endoscope 30 so that the portion surrounded by the guide frame 75 spreads to the full extent of the endoscope image 49.

As illustrated in FIG. 1D, when the guide frame 75 substantially matches the edge of the endoscope image 49, the endoscope image 49 is recorded as a still image. The still image may be generated by cutting out data of one frame from the moving image being observed in real time, or may be photographed using illumination and a shutter speed suitable for the still image separately from the moving image.

The recording of the still image may be automatically performed or may be performed based on an instruction from a doctor who has confirmed the state of the guide frame 75. Thereafter, the doctor appropriately operates the endoscope 30 toward the next region to be photographed.

By repeating the above operation, a series of still images corresponding to the reference image defined in the guidelines is recorded. In the process of operating the endoscope 30 so as to match the guide frame 75 and the endoscope image 49, the doctor can sufficiently visually observe the region to be photographed. Therefore, it is possible to prevent overlooking of the lesion.

Since a series of endoscope images 49 is recorded at a position, an orientation, and a size in accordance with the reference image, so-called double check in which an endoscope specialist doctor or the like confirms the recorded image can be efficiently performed.

Note that, in a case where a lesion is found during the endoscopic examination, the doctor performs observation necessary for detailed diagnosis out of the guidelines, and also performs endoscopic treatment in some cases. In such a case, the guide frame 75 is unnecessary. The doctor records the appropriate endoscope image 49 based on professional determination.

Figure 2:
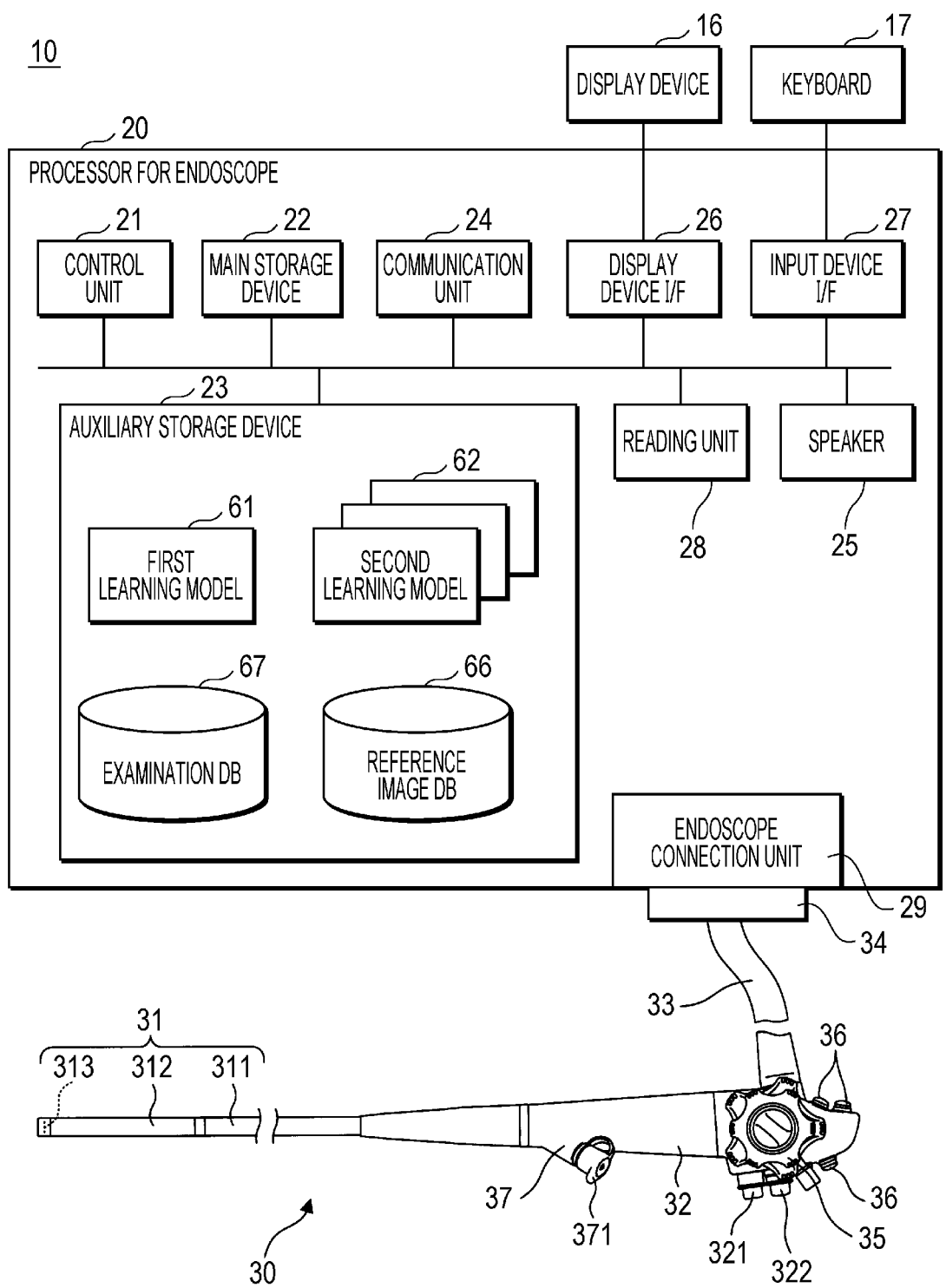
FIG. 2 is an explanatory diagram for explaining the configuration of the endoscope system.

FIG. 2 is an explanatory diagram for explaining the configuration of an endoscope system 10. The endoscope system 10 includes the endoscope 30, the processor for an endoscope 20. The processor for an endoscope 20 includes a control unit 21, a main storage device 22, an auxiliary storage device 23, a communication unit 24, a speaker 25, a display device interface (I/F) 26, an input device I/F 27, a reading unit 28, an endoscope connection unit 29, and a bus.

In FIG. 2, the illustration and description of the configuration that realizes the basic functions of the processor for an endoscope 20 such as the light source, the air/water supply pump, the suction pump, and the control unit of the image sensor provided at the distal end of the endoscope 30, are omitted.

The control unit 21 is an arithmetic control device that executes a program of the present embodiment. One or more central processing units (CPUs), graphics processing units (GPUs), or multi-core CPUs, and the like are used for the control unit 21. The control unit 21 is connected to each hardware unit constituting the processor for an endoscope 20 via a bus.

The main storage device 22 is a memory device such as a static random access memory (SRAM), a dynamic random access memory (DRAM), and a flash memory. The main storage device 22 temporarily stores information necessary in the middle of processing performed by the control unit 21 and a program being executed by the control unit 21.

The auxiliary storage device 23 is a memory device such as an SRAM, a flash memory, or a hard disk. The auxiliary storage device 23 includes a first learning model 61, a second learning model 62, a reference image DB 66, an examination DB 67, a program to be executed by the control unit 21, and various data necessary for executing the program.

The first learning model 61, the second learning model 62, the reference image DB 66, and the examination DB 67 may be stored in an external mass storage device connected to the processor for an endoscope 20.

The communication unit 24 is an interface that performs data communication between the processor for an endoscope 20 and a hospital information system (HIS) or the like. The speaker 25 outputs sound based on an instruction from the control unit 21.

The display device I/F 26 is an interface that connects the processor for an endoscope 20 and a display device 16. The input device I/F 27 is an interface that connects the processor for an endoscope 20 and an input device such as a keyboard 17. Note that the display device 16 and the input device may be configured integrally with the processor for an endoscope 20. The plurality of display devices 16 and the input device may be connected to the processor for an endoscope 20.

The endoscope 30 includes an insertion portion 31, an operation unit 32, a universal cord 33, and a connector unit 34. The operation unit 32 includes a bending knob 35, three switch buttons 36, a channel inlet 37, an air/water supply button 321, and a suction button 322. A forceps plug 371 having an insertion port for inserting a treatment instrument or the like is fixed to the channel inlet 37.

The insertion portion 31 is long and has one end connected to the operation unit 32 via a bend preventing portion. The insertion portion 31 includes a soft portion 311, a bending section 312, and a distal end portion 313 in this order from the operation unit 32. The distal end portion 313 is provided with an observation window and an illumination window, and an image sensor is disposed behind the observation window. The bending section 312 is bent according to an operation of the bending knob 35.

Hereinafter, the longitudinal direction of the insertion portion 31 is referred to as an "insertion direction". Similarly, a side close to the operation unit 32 along the insertion direction is referred to as an operation unit side, and a side distant from the operation unit 32 is referred to as a distal end side.

The universal cord 33 is long, and has a first end connected to the operation unit 32 and a second end connected to the connector unit 34. The universal cord 33 is soft. The connector unit 34 is detachably coupled to the endoscope connection unit 29 provided in the processor for an endoscope 20.

The switch button 36 is connected to the processor for an endoscope 20 via a cable (not illustrated) and the connector unit 34. Among various functions of the processor for an endoscope 20, necessary operations during the endoscopic examination can be assigned to the switch buttons 36. By using the switch buttons 36, the doctor can perform a necessary operation without releasing the hand from the endoscope 30.

In the present embodiment, the switch button 36 to which a so-called release function of recording the endoscope image 49 as a still image is allocated is described as an image capturing button. When the doctor as the user presses the image capturing button, the control unit 21 promptly records the still image in the examination DB 67. In the following description, recording a still image in examination DB 67 may be referred to as "photographing".

FIG. 3 is an explanatory diagram for explaining a record layout of the reference image DB 66. The reference image DB 66 is a DB in which the photographing sequence according to the guidelines, the region name, and the reference image are recorded in association with each other. The reference image DB 66 includes a photographing sequence field, a region name field, and a reference image field.

In the photographing sequence field, the photographing sequence according to the guidelines is recorded. In the region name field, the name of the region to be photographed determined for capturing an image according to the guidelines is recorded. In the reference image field, a reference image recommended in the guidelines is recorded. The reference image DB 66 has one record for one region to be photographed.

FIG. 4 is an explanatory diagram for explaining a record layout of the examination DB 67. The examination DB 67 is a DB in which the name of the region to be photographed obtained by capturing an image in the endoscopic examination, similarity between the captured image and the reference image, and the recorded image are recorded in association with each other. The examination DB 67 includes a doctor identifier (ID) field, a medical examinee ID field, a date field, a number field, a region name field, a similarity field, and an image field.

In the doctor ID field, a doctor ID uniquely assigned to a doctor in charge of the endoscopic examination is recorded. In the medical examinee ID field, a medical examinee ID uniquely assigned to a medical examinee who has undergone an endoscopic examination is recorded. A date is recorded in the date field. In the number field, numbers assigned in ascending order to the still images recorded during the endoscopic examination are recorded.

In the region name field, the name of the region to be photographed defined in the guidelines is recorded. "-" indicates the image captured by the determination of the doctor separately from the guidelines and the reference image. The similarity with the reference image is recorded in the similarity field. "-" means that the similarity is not calculated because there is no reference image. In the image field, a file of still images is recorded.

The outline of the similarity recorded in the similarity field will be described. The similarity is a numerical value obtained by quantifying the degree of similarity between two images. In the present embodiment, the similarity is expressed by a numerical value from 0 to 100, where the degree is 0 when there is no match and 100 when there is a complete match, but the similarity is not limited thereto.

Various methods have been conventionally used to quantify the similarity between two images. For example, for each of two images, a feature amount vector is generated based on various feature amounts such as color distribution and positions of feature points. The larger the distance between the feature amount vectors, the lower the similarity, and the smaller the distance between the feature vectors, the higher the similarity.

The feature amount vector may be generated using a learning model for image classification. As the learning model for image classification, for example, a learned convolutional neural network (CNN) model such as the VGG 16 or the VGG 19 can be used. A learned model obtained by being caused to additionally learn the endoscope image 49 for these CNN models may be used. The two images are input to the learning model for image classification, and an output from each node of the output layer is used as a feature amount vector of each image.

When the endoscope image 49 is input, the similarity may be calculated using a learning model in which a parameter is adjusted so as to output the similarity with the reference image. For example, a probability that the reference image and the endoscope image 49 are the identical image is used as the reference degree. In this case, a learning model for similarity calculation is generated for each reference image.

The similarity may be calculated based on a bounding box indicating a predetermined target extracted from the endoscope image 49 using an object detection method such as regions with convolutional neural networks (R-CNN). For example, it is determined that the similarity is high when the area in which the bounding box which extracts the cardiac region overlaps with the bounding box indicating the cardiac region on the reference image is large.

A probability when a predetermined target is detected using an object detection method such as the R-CNN may be used as the similarity.

The data recorded in the examination DB 67 may be appropriately uploaded to an electronic medical record system or the like.

Figure 5:
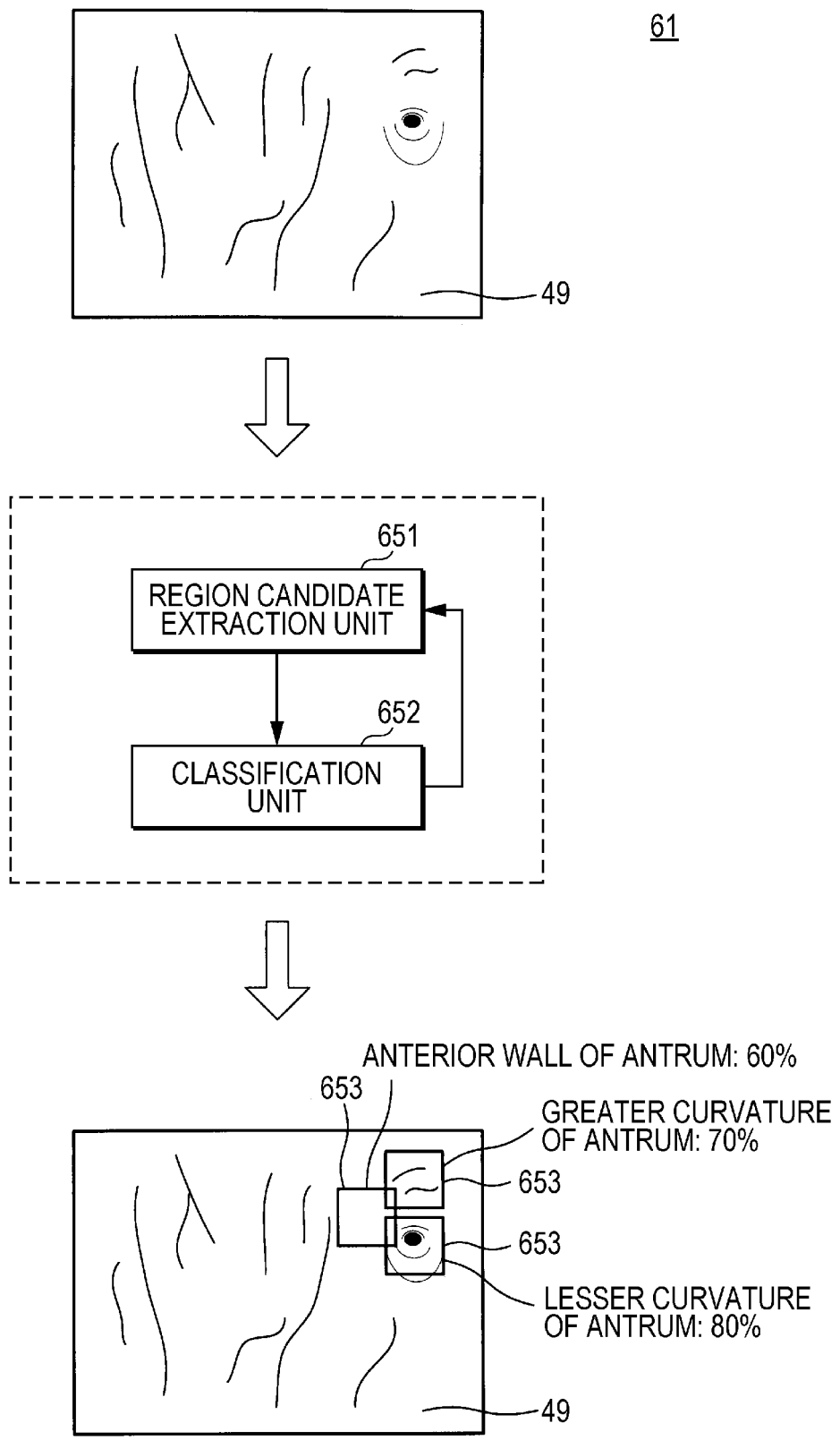
FIG. 5 is an explanatory diagram for explaining a configuration of a first learning model.

FIG. 5 is an explanatory diagram for explaining a configuration of the first learning model 61. The first learning model 61 is a learning model that receives an input of the endoscope image 49 to output, a region similar to a region to be photographed defined in the guidelines, that is the reference image. FIG. 5 illustrates an example of the first learning model 61 using the R-CNN.

The first learning model 61 includes a region candidate extraction unit 651, a classification unit 652, and a neural network (not illustrated). The neural network includes a convolutional layer, a pooling layer, and a fully-connected layer. The endoscope image 49 is input to the first learning model 61.

The region candidate extraction unit 651 extracts, from the input endoscope image 49, region candidates of various sizes are extracted. The classification unit 652 calculates a feature amount of the extracted region candidate, and classifies the object appearing in the region candidate based on calculated feature amount. The target to be classified here is each region to be photographed defined in the guidelines. The first learning model 61 repeats extraction and classification of region candidates, and determines a target region including a region to be photographed appearing in each portion of the endoscope image 49 for which an input has been received.

In FIG. 5, the first learning model 61 outputs information about a target region indicated by three detection frames (bounding boxes) 653. In the example illustrated in FIG. 5, a target region in which the lesser curvature of antrum appears with a probability of 80%, a target region in which the greater curvature of antrum appears with a probability of 70%, and a target region in which the anterior wall of antrum appears with a probability of 60% are output.

An outline of a method of generating the first learning model 61 will be described. The first learning model 61 is generated using a plurality of pieces of training data in which the endoscope image 49 in which a lesion does not appear and the name, position, and range of the region to be photographed included in the endoscope image 49 are recorded in association with each other. Specifically, when the endoscope image 49 in the training data is input, the parameters of the neural network are adjusted by an error back propagation method so that the data output from the classification unit 652 matches the name, position, and range of the region to be photographed in the training data.

Figure 6:
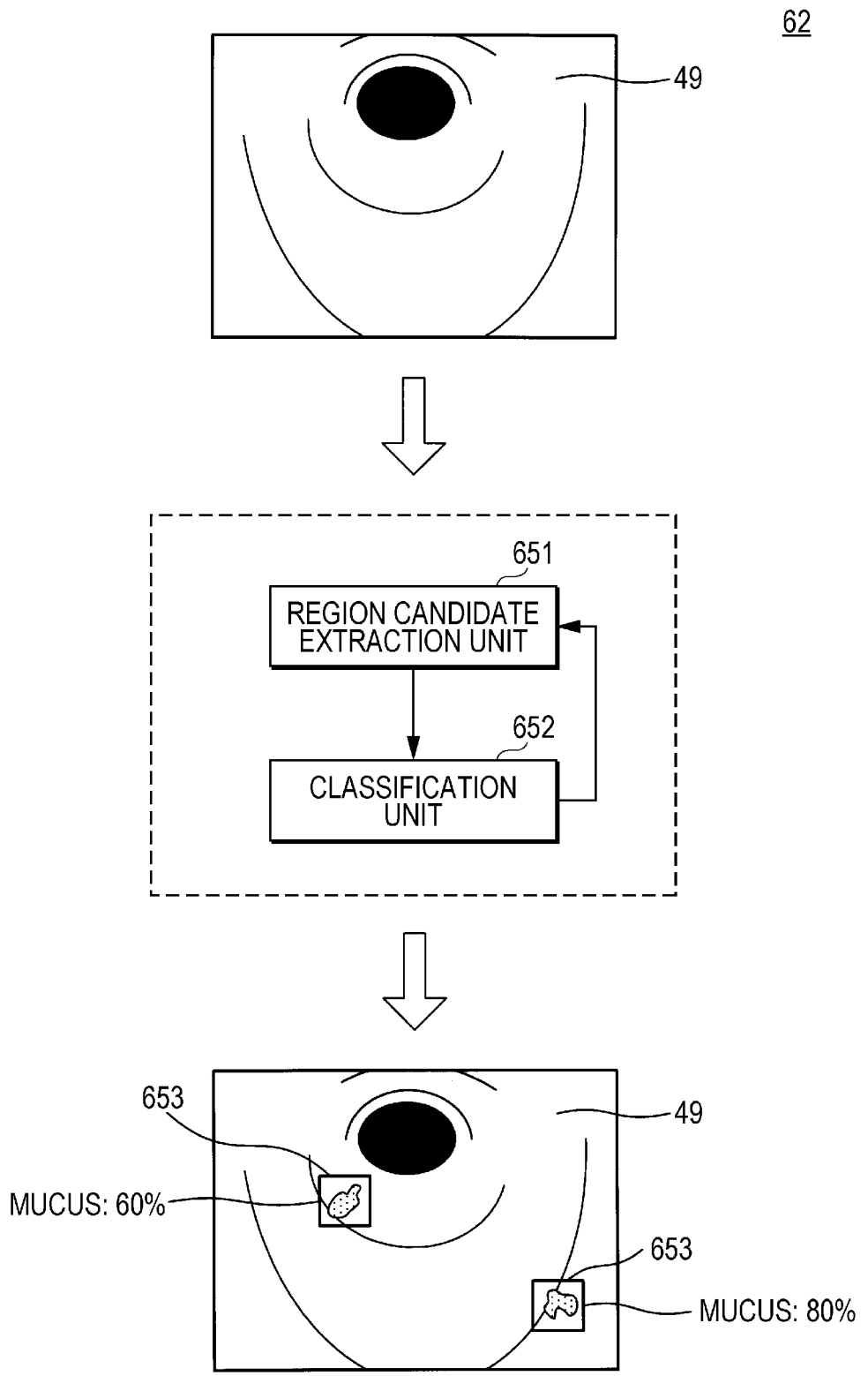
FIG. 6 is an explanatory diagram for explaining a configuration of a second learning model.

FIG. 6 is an explanatory diagram for explaining a configuration of the second learning model 62. The second learning model 62 is a learning model that receives an input of the endoscope image 49 and outputs a region in which the foreign matter such as mucus and residues appears. FIG. 6 illustrates an example of the second learning model 62 using the R-CNN.

The second learning model 62 includes the region candidate extraction unit 651, the classification unit 652, and a neural network (not illustrated). The neural network includes a convolutional layer, a pooling layer, and a fully-connected layer. The endoscope image 49 is input to the second learning model 62.

The region candidate extraction unit 651 extracts, from the input endoscope image 49, region candidates of various sizes are extracted. The classification unit 652 calculates a feature amount of the extracted region candidate, and classifies the object appearing in the region candidate based on calculated feature amount. The target to be classified here is foreign matter such as mucus and residues. The second learning model 62 repeats extraction and classification of region candidates, and determines the foreign matter appearing in each portion of the endoscope image 49 that has received an input.

In FIG. 6, the second learning model 62 outputs information about the regions indicated by the two detection frames 653. In the example illustrated in FIG. 6, a region in which mucus appears with a probability of 80%, and a region in which mucus appears with a probability of 60% are output.

The second learning model 62 is created for each reference image. Before photographing the endoscope image 49 corresponding to the reference image, the control unit 21 uses the second learning model 62 to determine whether there is a region in which the foreign matter appears. In a case where the foreign matter appears, the control unit 21 outputs a notification for calling user's attention. After a doctor who is a user removes the foreign matter using, for example, a sub water supply function of the endoscope 30, the control unit 21 photographs a still image.

An outline of a method of generating the second learning model 62 will be described. The second learning model 62 is generated by using a plurality of pieces of training data in which the endoscope image 49 obtained by photographing the region to be photographed and the type, position, and range of the foreign matter appearing in the endoscope image 49 are recorded in association with each other. Specifically, when the endoscope image 49 in the training data is input, the parameters of the neural network are adjusted by an error back propagation method so that the data output from the classification unit 652 matches the type, position, and range of the foreign matter in the training data.

Note that the second learning model 62 may be a learned model so as to output a region in which a lesion such as a cancer, an ulcer, a polyp, or a bleeding portion appears. In this case, the second learning model 62 is generated using the training data in which the type, position, and range of the lesion are recorded in association with each other in addition to the foreign matter.

Note that, instead of the R-CNN, any object detection algorithm such as Fast R-CNN, Faster R-CNN, Mask R-CNN, Single Shot Multibook Detector (SSD), or You Only Look Once (YOLO) may be used.

One learning model in which the first learning model 61 and the second learning model 62 are integrated may be used. In this case, the learning model receives an input of the endoscope image 49 to output both a region similar to the reference image corresponding to the reference image and the foreign matter in the endoscope image.

Figure 7:
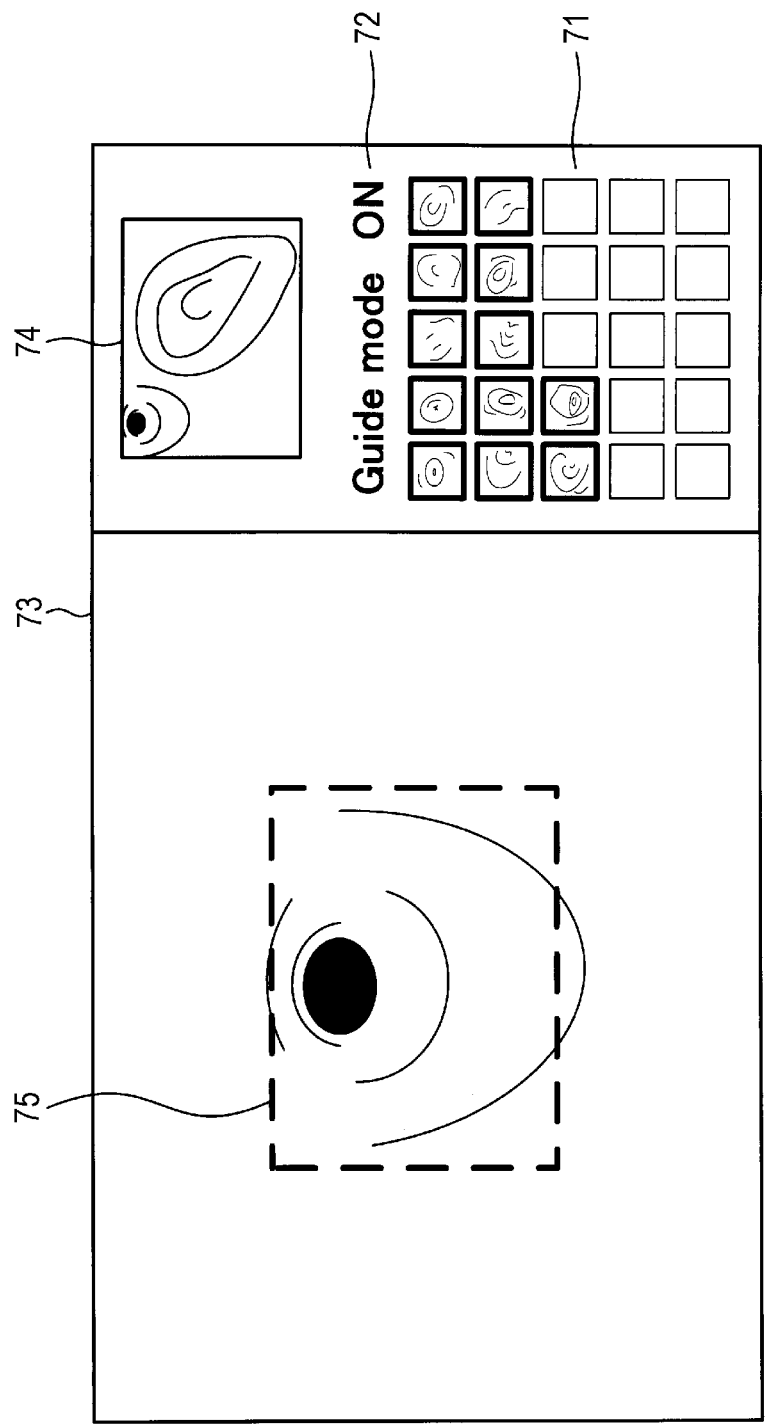
FIG. 7 is an explanatory diagram for explaining a screen display example.

FIGS. 7 to 16 are explanatory diagrams for explaining screen display examples. FIG. 7 illustrates an example of a screen displayed on the display device 16 by the control unit 21 when a region including the next region to be photographed is output by the first learning model 61.

The screen illustrated in FIG. 7 includes an endoscope image field 73, a progress display field 71, a state display field 72, and a past image field 74. The control unit 21 displays the endoscope image 49 in the endoscope image field 73 in real time. The control unit 21 displays the guide frame 75 which is superimposed on the endoscope image 49. The guide frame 75 is an index indicating a rough indication of a contour of an image when the next region to be photographed is photographed with the composition same as that of the reference image.

The control unit 21 displays the endoscope image 49 captured in the past in the progress display field 71 as a thumbnail. In FIG. 7, thumbnails are displayed in portions surrounded by thick frames. The portion surrounded by the narrow frame is blank. That is, by displaying the thumbnail of the progress display field 71, the control unit 21 functions as a first notification output unit that outputs a notification when the endoscope image 49 is recorded.

The reference image may be displayed in a portion surrounded by a narrow frame. In this case, the control unit 21 displays the captured endoscope image 49 and the reference image so as to be distinguishable from each other by, for example, the thickness, color, or the like of a frame line surrounding the periphery of the thumbnail.

When accepting the selection of the thumbnail, the control unit 21 pops up a large image. Since a method of generating thumbnails and displaying the thumbnails in a list and a method of displaying the thumbnails in a pop-up are conventionally used, the description thereof will be omitted.

The control unit 21 displays the operating mode in the state display field 72. "Guide Mode ON" means a mode for displaying the guide frame 75 indicating the next region to be photographed. Even when the next region to be photographed does not appear in the endoscope image 49 and the guide frame 75 is not displayed, the user can confirm the operating mode by viewing the state display field 72.

In the past image field 74, an endoscope image 49 captured immediately before is displayed. Note that an image selected by the user from the thumbnails displayed in the progress display field 71 may be displayed in the past image field 74.

The user operates the endoscope 30 so that the guide frame 75 and the outer periphery of the endoscope image field 73 match with each other. With this operation, the user adjusts the endoscope image 49 to magnification and layout similar to those of the reference image.

Note that the name and the like of the corresponding region to be photographed may be displayed in the vicinity of the guide frame 75. By referring to arrows or the like from the four corners of the endoscope image 49 toward the corners of the guide frame 75, the display indicating that the endoscope 30 should be operated to make the guide frame 75 large may be performed.

Figure 8:
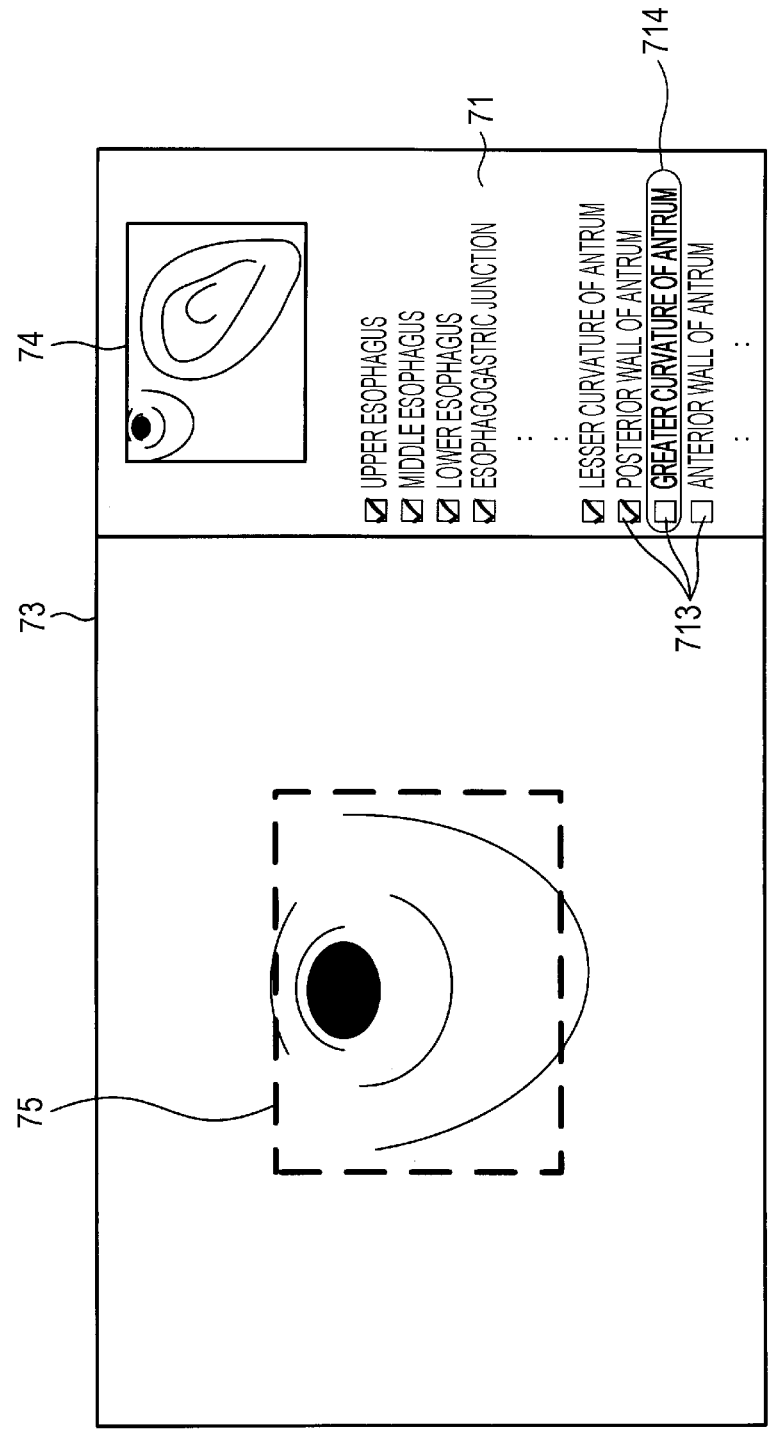
FIG. 8 is an explanatory diagram for explaining a screen display example.

FIG. 8 is an example of a screen displayed instead of FIG. 7. On the screen illustrated in FIG. 8, the control unit 21 displays a list of the names of the regions to be photographed defined in the guidelines in the progress display field 71. The control unit 21 displays a check box 713 on the left side of each name. A checked check box 713 means that the image has been captured. That is, by the display of the check box 713, the control unit 21 functions as a first notification output unit that outputs a notification when the endoscope image 49 is recorded.

The control unit 21 displays the name of the next region to be photographed surrounded by a frame index 714. In the mode in which the guide frame 75 is not displayed, the control unit 21 does not display the frame index 714. Therefore, even when the state display field 72 is not displayed, the user can confirm the operating mode.

The user can set whether to use the screen described with reference to FIG. 7 or the screen described with reference to FIG. 8. The control unit 21 displays a screen based on selection by the user. Note that the screen described with reference to FIGS. 7 and 8 is an example. The control unit 21 may display a screen of a design other than these.

Figure 9:
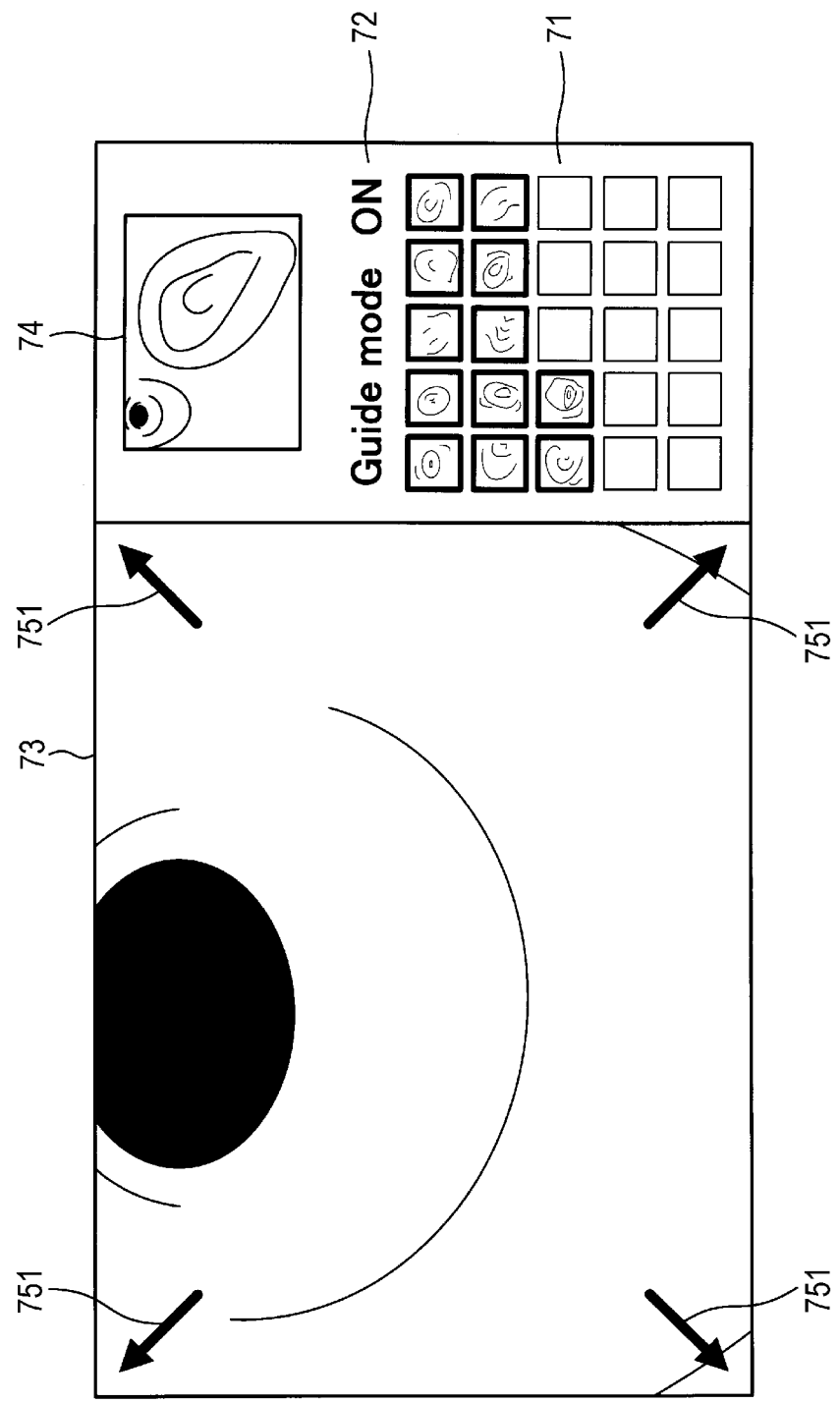
FIG. 9 is an explanatory diagram for explaining a screen display example.

FIG. 9 is an example of a screen in a state where the distal end portion 313 is too close to the region to be photographed and the guide frame 75 is not displayed. The control unit 21 indicates that the guide frame 75 is outside the endoscope image field 73 by the arrow-like approach index 751 displayed at the four corners of the endoscope image field 73.

Note that, instead of displaying the arrow, the control unit 21 may display characters such as "too close" above the state display field 72, for example. It is possible to prevent the endoscope image 49 from being hidden by the arrow.

Figure 10:
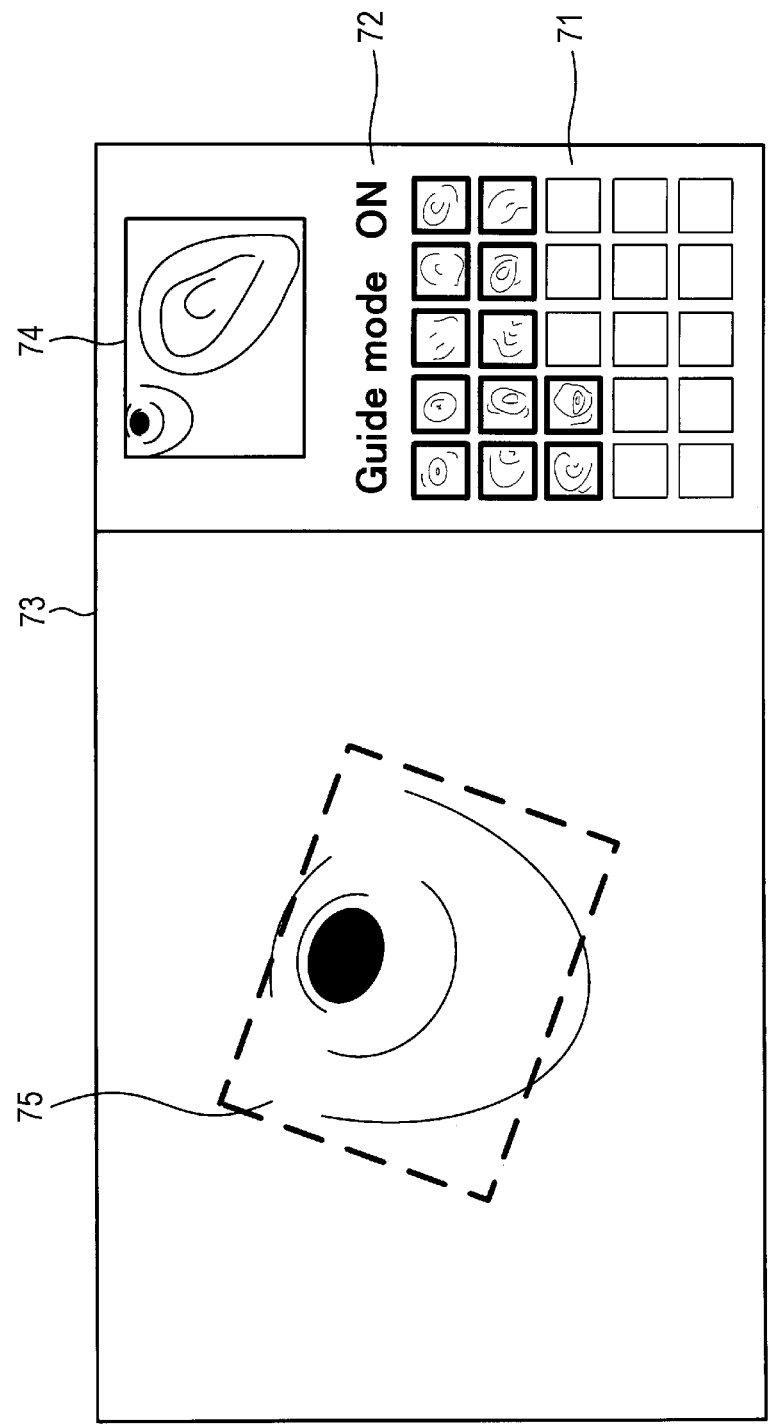
FIG. 10 is an explanatory diagram for explaining a screen display example.

FIG. 10 is an example of a screen in a case where the distal end portion 313 approaches the region to be photographed but the endoscope image 49 rotates with respect to the reference image. The control unit 21 performs matching so that the similarity between the endoscope image 49 inside the guide frame 75 and the reference image is high in a case where the guide frame 75 approaches the edge of the endoscope image field 73. When the endoscope image 49 is rotated with respect to the reference image, the guide frame 75 is displayed in a state of being rotated with respect to the edge of the endoscope image field 73 as illustrated in FIG. 10.

The user performs a twisting operation of the insertion portion 31 while bringing the distal end portion 313 close to the observation target region, thereby matching the guide frame 75 with the outer periphery of the endoscope image field 73.

Figure 11:
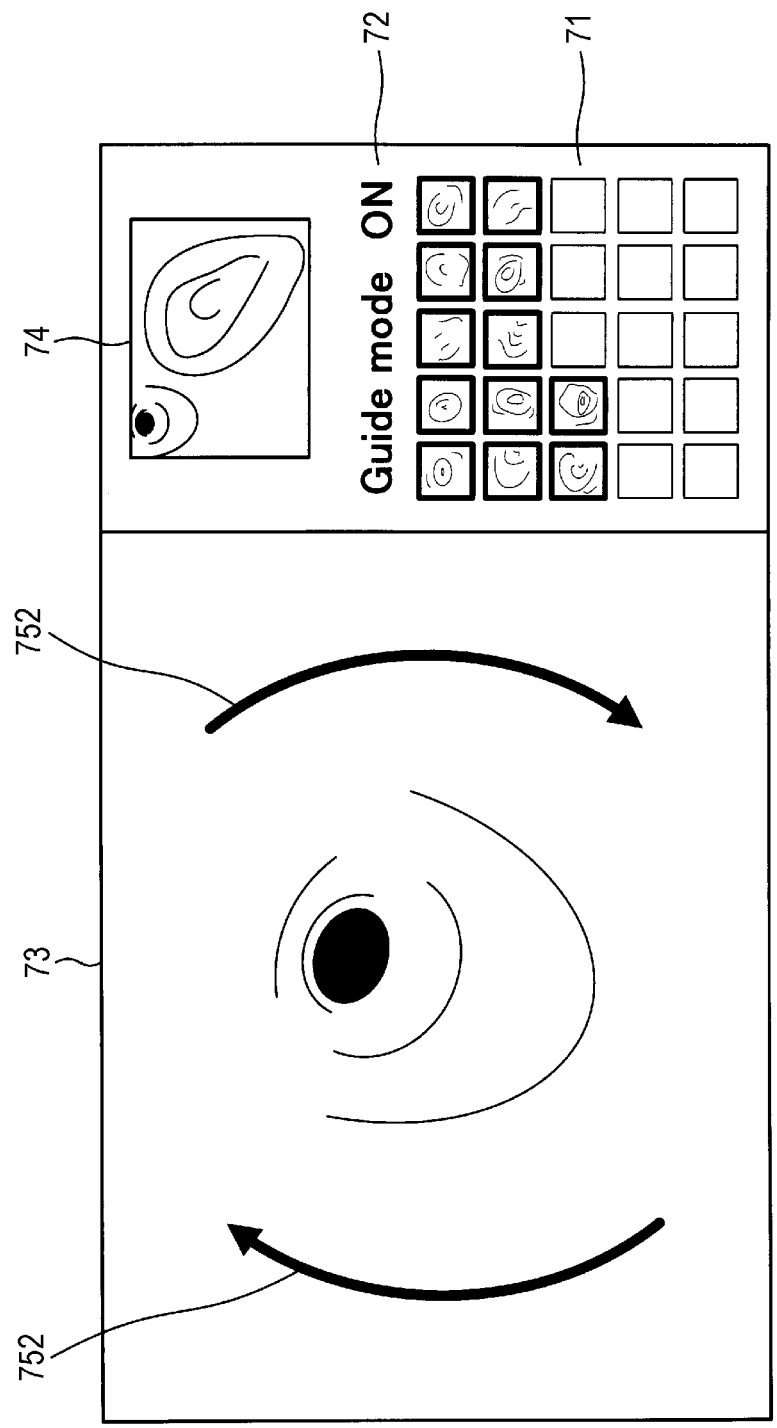
FIG. 11 is an explanatory diagram for explaining a screen display example.

FIG. 11 illustrates a modification of the screen in a case where the endoscope image 49 rotates with respect to the reference image similarly to FIG. 10. Instead of displaying the guide frame 75 in a state of being rotated with respect to the edge of the endoscope image field 73, the control unit 21 displays the rotation index 752 indicating the rotation direction with the index superimposed the endoscope image 49. The user performs a twisting operation of the insertion portion 31 with reference to the rotation index 752.

Figure 12:
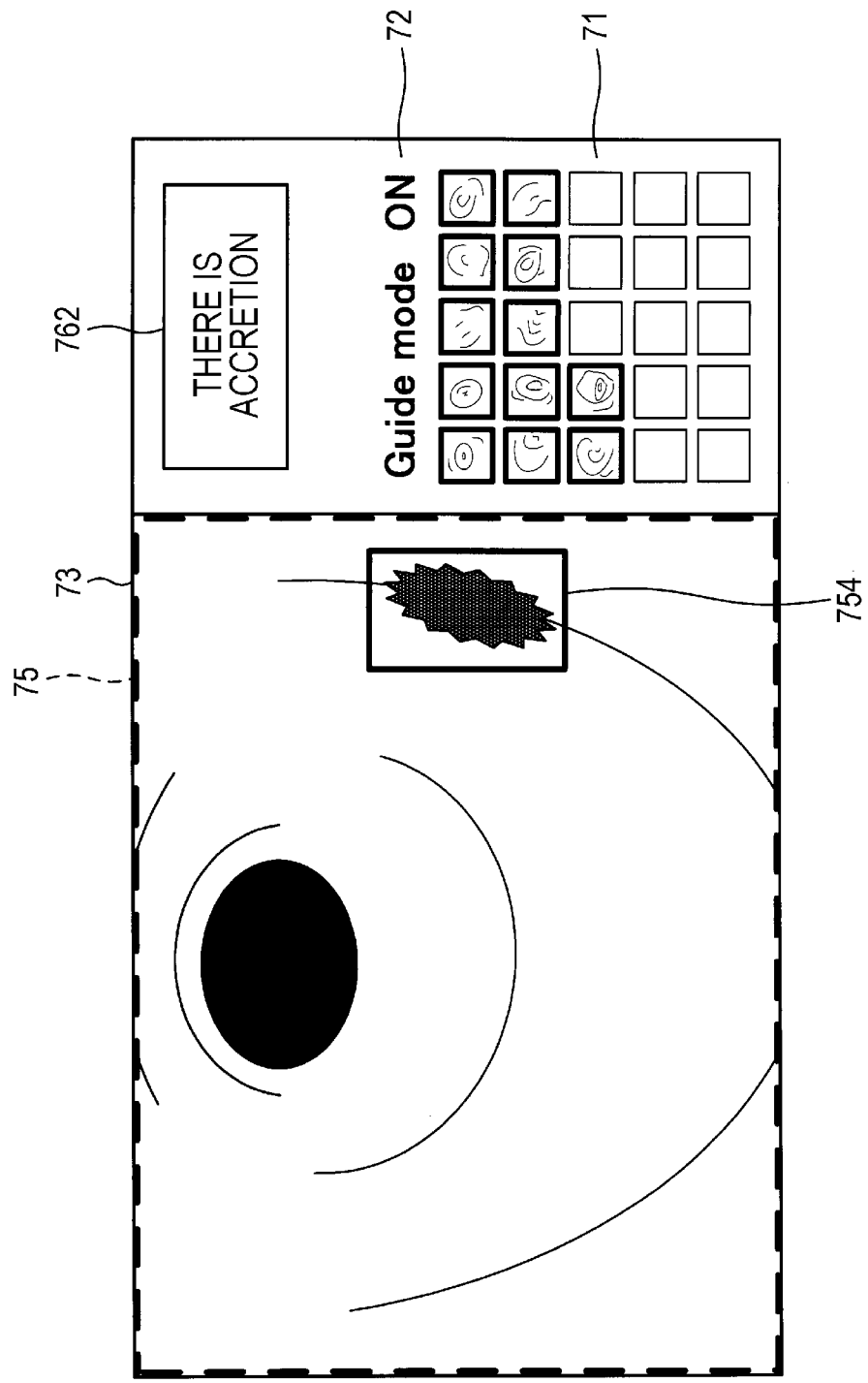
FIG. 12 is an explanatory diagram for explaining a screen display example.

FIG. 12 is an example of a screen in a case where an accretion such as mucus exists in the region to be photographed. In a case where the guide frame 75 and the outer periphery of the endoscope image field 73 substantially match with each other, the control unit 21 inputs the endoscope image 49 to the second learning model 62 and acquires a region where an accretion exists. In a case where an accretion exists, the control unit 21 displays an accretion frame 754 indicating the accretion with the frame superimposed on the endoscope image 49. The control unit 21 displays an accretion mark 762 instead of the past image field 74. The user removes the accretion using the sub water supply function or the like of the endoscope 30.

Figure 13:
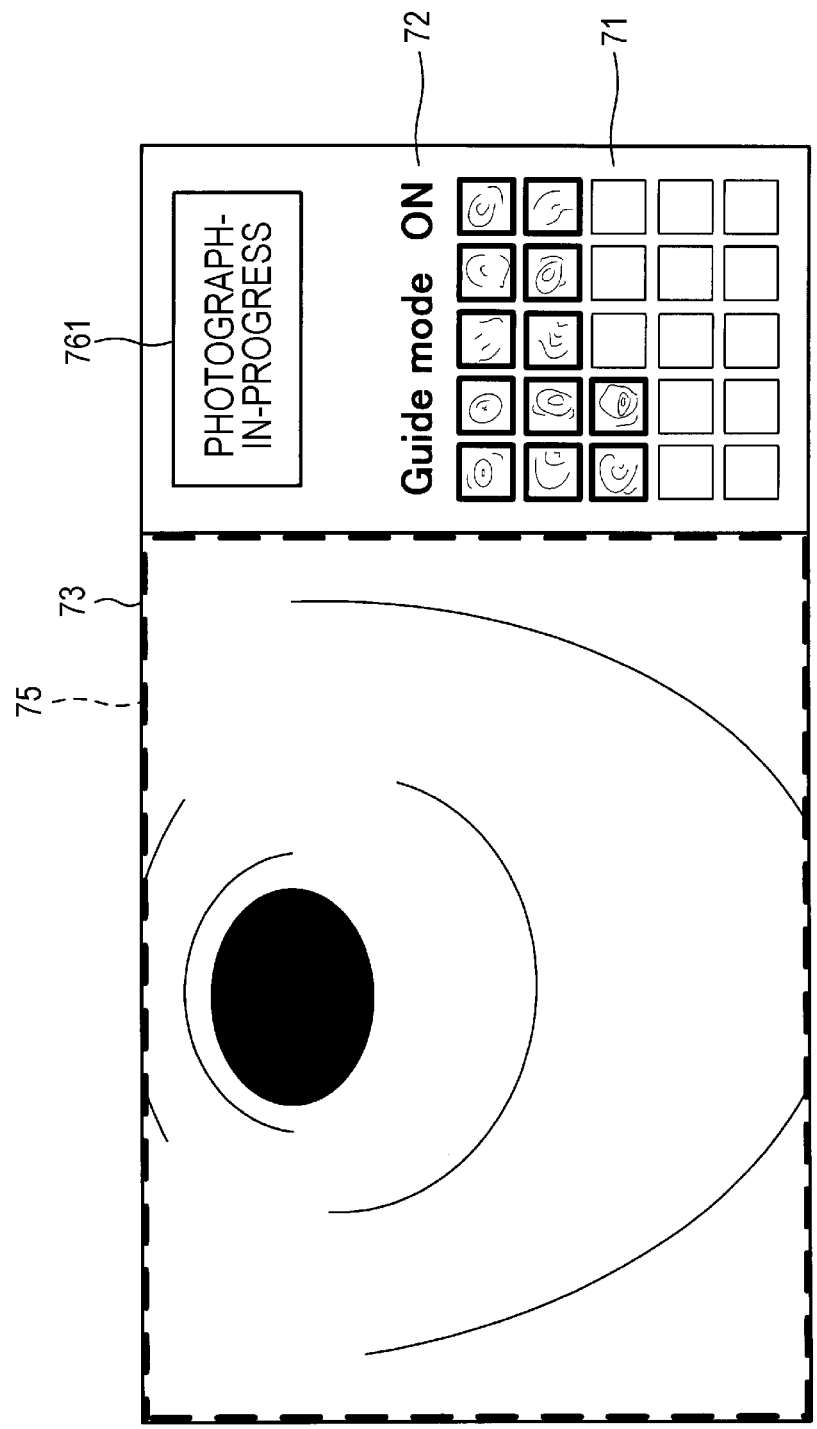
FIG. 13 is an explanatory diagram for explaining a screen display example.

FIG. 13 is an example of a screen being captured. The user matches the guide frame 75 with the outer periphery of the endoscope image field 73, confirms that there is no accretion, and then stops the distal end portion 313 to prevent image blurring. The control unit 21 displays a photograph-in-progress index 761 and photographs the endoscope image 49. As described above, the endoscope image 49 without blurring is photographed with the magnification and layout same as those of the reference image.

When photographing is completed, the control unit 21 outputs a notification sound from the speaker 25. The control unit 21 may notify the similarity between the captured endoscope image 49 and the reference image by sound as illustrated in Table 1.

[Table 1]

In a case where photographing of the endoscope image having high similarity continues, the notification sound of the major code continues, so that the user can proceed with the endoscopic examination comfortably. On the other hand, in a case where photographing of an endoscope image having low similarity continues, attention of the user can be attracted by the minor code and a single sound.

Note that the notification sounds shown in Table 1 are examples. In a case where the similarity is high, a sound emphasizing a sense of success, such as a sound of "pin-pong" or a melody preferred by the user, may be used as the notification sound. In a case where the similarity is not high, a sound expressing progress, such as "beep" or "honk", may be used. It is desirable that the user can appropriately set the presence or absence and the volume of the notification sound.

Figure 14:
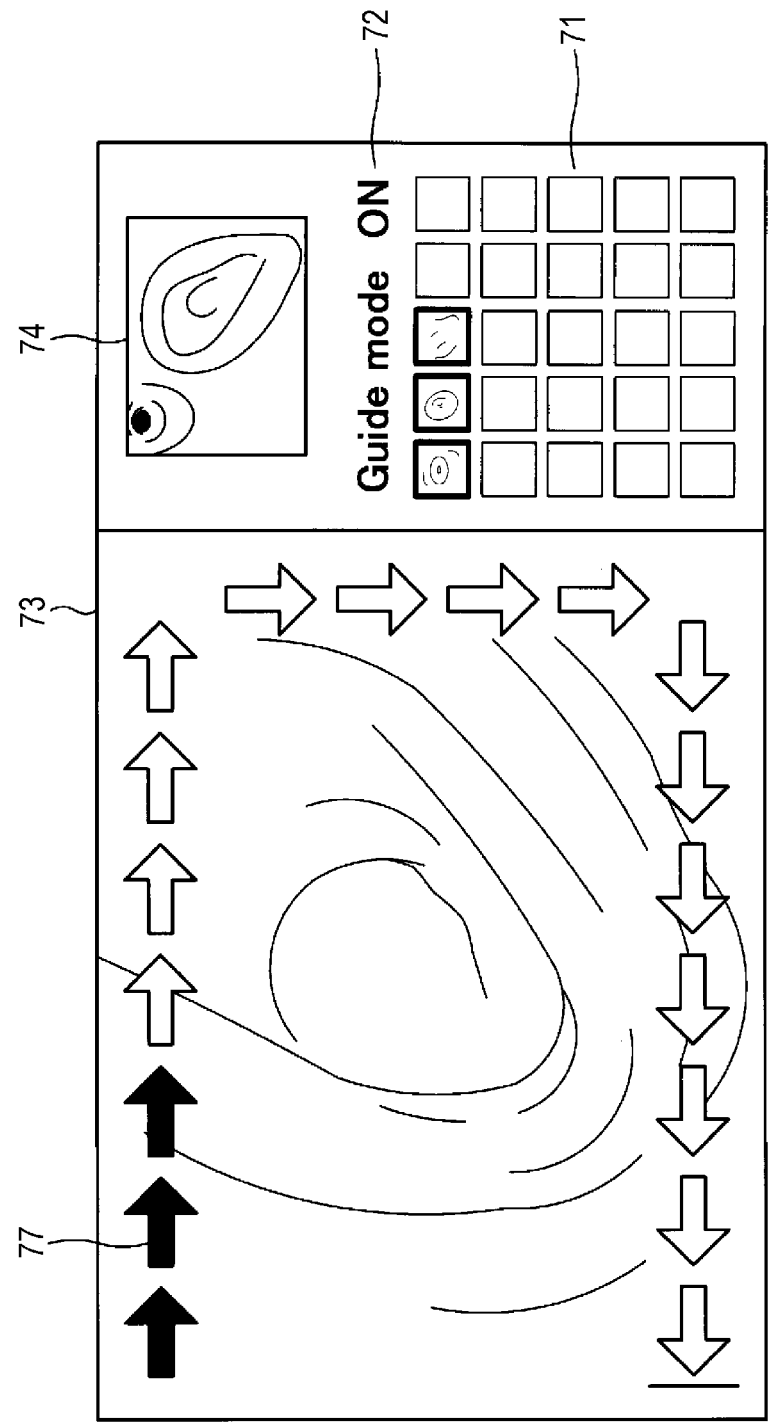
FIG. 14 is an explanatory diagram for explaining a screen display example.

FIG. 14 is a modification of a screen displayed in a case where the next region to be photographed does not appear in the endoscope image 49 and the guide frame 75 is not displayed. The control unit 21 displays a guide-in-progress mark 77 in which thick arrows are disposed along the outer periphery of the endoscope image field 73. The total number of thick arrows indicates the total number of still images to be photographed. The black thick arrow indicates the number of captured still images. In the example illustrated in FIG. 14, 3 of 18 images have been captured.

Since the guide-in-progress mark 77 is displayed in addition to the progress display field 71 and the state display field 72, the user can easily confirm that the mode is a mode in which the guide frame 75 is to be displayed while being conscious of the progress of the examination. In a case where the guide frame 75 is not displayed, the control unit 21 may display the guide-in-progress mark 77 on a steady basis or may display the guide-in-progress mark 77 intermittently.

Since the guide-in-progress mark 77 is displayed in addition to the state display field 72, the user can easily confirm that the mode is a mode in which the guide frame 75 is to be displayed.

Figure 15:
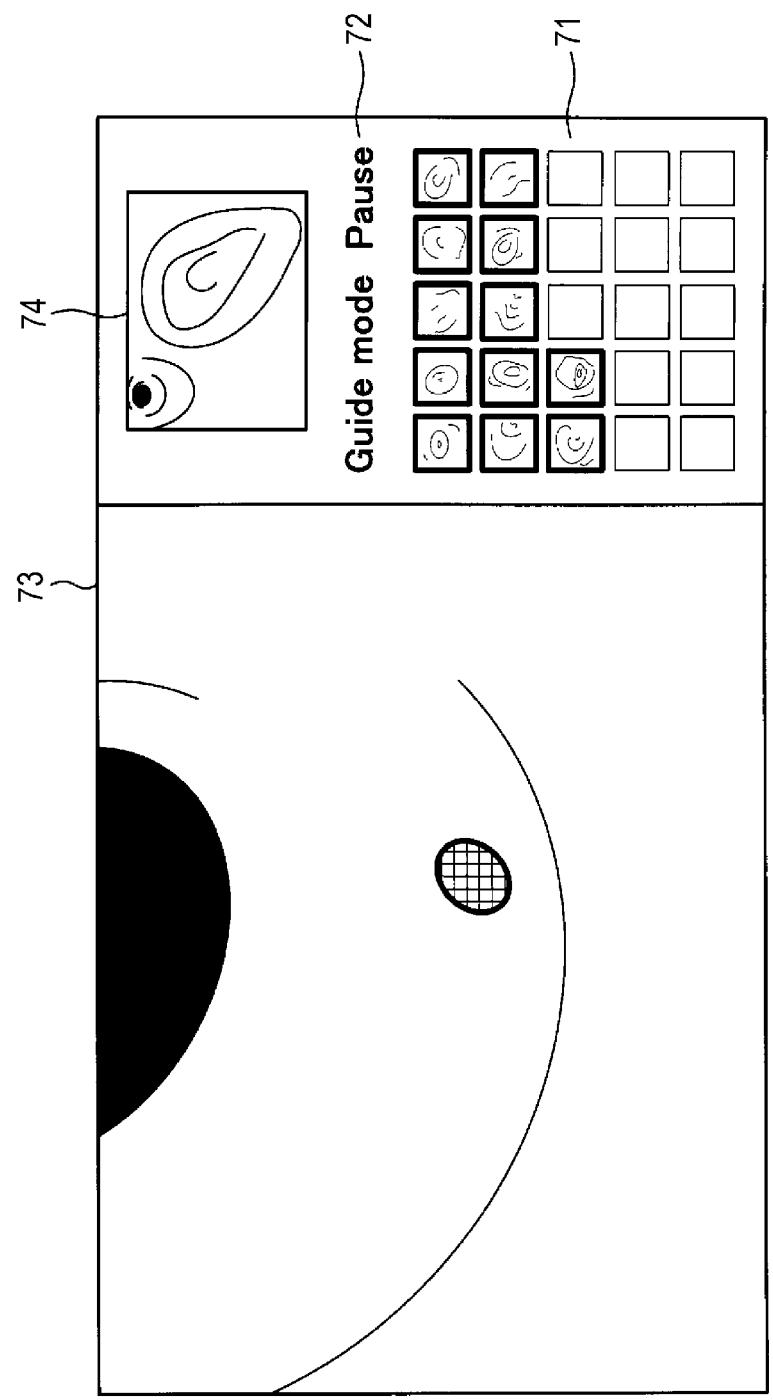
FIG. 15 is an explanatory diagram for explaining a screen display example.

FIG. 15 is an example of a screen displayed in a case where the user performs observation deviating from the guidelines. In FIG. 15, a lesion region is indicated by grid-like hatching. For example, in a case where the user starts special light observation, in a case where the user starts enlargement observation using a zoom function, in a case where the user scatters a pigment, or the like, the control unit 21 determines that observation deviating from the guidelines is started.

The control unit 21 displays "Guide Mode Pause" in the state display field 72, which means a mode for stopping the display of the guide frame 75. The control unit 21 stops display of the guide frame 75. As a result, the user can observe the entire endoscope image 49 without being obstructed by the guide frame 75.

Figure 16:
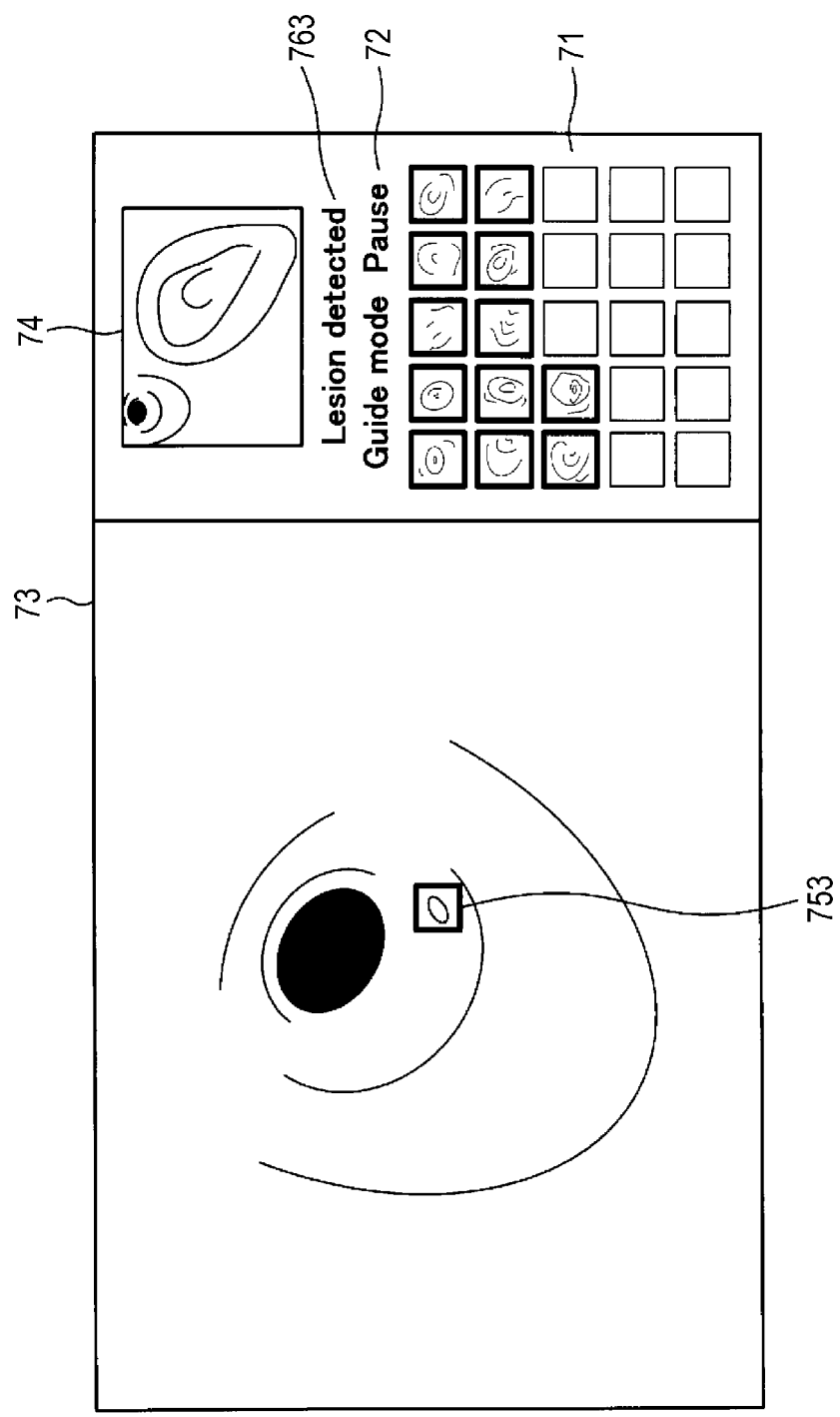
FIG. 16 is an explanatory diagram for explaining a screen display example.

FIG. 16 illustrates an example of a screen displayed when the control unit 21 detects a lesion. Software or the like for detecting a lesion such as a cancer or a polyp in real time from the endoscope image 49 has already been used, and thus a detailed description thereof will be omitted.

When a lesion is detected, the control unit 21 stops displaying the guide frame 75 and displays a lesion frame 753 surrounding the lesion. The control unit displays a detection notification field 763 for notifying that a lesion has been detected. The control unit 21 displays "Guide Mode Pause" in the state display field 72, which means a mode for stopping the display of the guide frame 75. The control unit 21 may output the notification sound from speaker 25. The user observes the detected lesion and performs appropriate treatment based on professional determination.

In a case where the screen described with reference to FIG. 15 or 16 is displayed, the control unit 21 receives an instruction to resume the mode for displaying the guide frame 75 from the user. For example, in a case where the user sufficiently observes the lesion and determines to continue the observation according to the guidelines, the user gives an instruction to change to a mode for displaying the guide frame 75 by an operation of the keyboard 17, voice input, or the like. The mode change instruction may be assigned to the switch button 36 different from the image capturing button.

Figure 17:
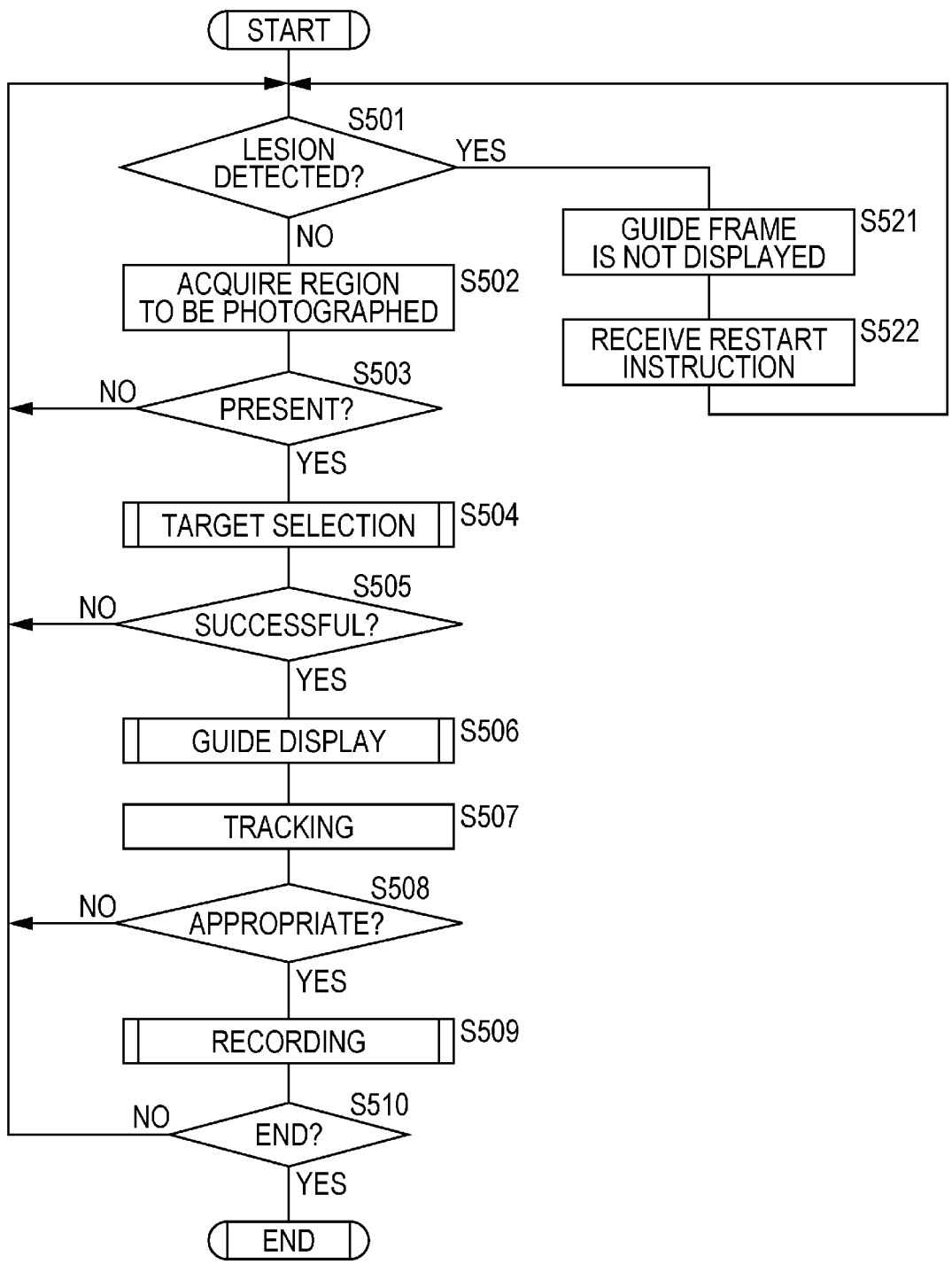
FIG. 17 is a flowchart for explaining a processing flow of a program.

FIG. 17 is a flowchart for explaining the processing flow of a program. The control unit 21 determines whether a lesion is detected (step S501). For example, in a case where an operation such as special light observation or enlargement observation is received, the control unit 21 determines that a lesion is detected.

The control unit 21 may determine whether a lesion is detected based on the endoscope image 49. For example, in a case where the color of the endoscope image 49 suddenly changes due to pigment spraying, in a case where the distal end of the treatment instrument appears in the endoscope image 49, or the like, the control unit 21 may determine that a lesion is detected. The control unit 21 may receive information indicating that a lesion has been detected in the endoscope image 49 from the lesion detection software.

The control unit 21 may determine that a lesion is detected when a treatment instrument is inserted into the channel. For example, the control unit 21 can detect insertion of a treatment instrument via a sensor provided in the channel inlet 37.

The control unit 21 may determine that a lesion is detected based on an instruction from the user received through the switch button 36, voice input, or the like. In a case where the user desires to observe the endoscope image 49 without being obstructed by the guide frame 75, the user can shift the mode to a mode in which the guide frame 75 is not displayed. In step S501, the control unit 21 realizes a function of a lesion detection unit that detects that a lesion is being observed.

When it is determined that no lesion is detected (NO in step S501), the control unit 21 inputs the endoscope image 49 to the first learning model 61 and acquires a region to be photographed (step S502). The control unit 21 determines whether there is a region to be photographed where the dimension of the detection frame 653 acquired from the first learning model 61 is larger than a predetermined value and a probability of exceeding a predetermined threshold value is output (step S503). When it is determined that there is no region to be photographed (NO in step S503), the control unit 21 returns to step S501.

When it is determined that there is the region to be photographed (YES in step S503), the control unit 21 activates a subroutine of target selection (step S504). The subroutine of the target selection is a subroutine of selecting the region to be photographed for displaying the guide frame 75 from the region to be photographed output from the first learning model 61. The return value of the subroutine of target selection includes a variable indicating whether the selection of the region to be photographed is successful. The processing flow of the subroutine of target selection will be described later.

The control unit 21 determines whether the subroutine of target selection has succeeded in selecting the region to be photographed (step S505). When it is determined that it is not successful (NO in step S505), the control unit 21 returns to step S501.

When it is determined that it is successful (YES in step S505), the control unit 21 starts the subroutine of the guide display (step S506). The subroutine of the guide display is a subroutine that displays the guide frame 75 superimposed on the endoscope image 49. The processing flow of the subroutine of the guide display will be described later.

The control unit 21 performs tracking of changing the display of the guide frame 75 in accordance with the change in the endoscope image 49 (step S507). The control unit 21 determines whether the endoscope image 49 is in an appropriate state for photographing the region to be photographed (step S508). Specifically, in a case where most of the area of the endoscope image 49, for example, 90% or more, is surrounded by the guide frame 75 being tracked, the control unit 21 determines that it is in an appropriate state.

When it is determined that it is in an appropriate state (YES in step S508), the control unit 21 activates a subroutine of a record (step S509). The subroutine of a record is a subroutine for recording the endoscope image 49 in the examination DB 67. The processing flow of the subroutine of a record will be described later.

The control unit 21 determines whether to end the process (step S510). For example, in a case where all the regions to be photographed defined in the guidelines have been photographed or in a case where the insertion portion 31 has been removed from the medical examinee, the control unit 21 determines that the process ends. When it is determined that the process ends (YES in step S510), the control unit 21 ends the process.

When it is determined that the process does not end (NO in step S510) or when it is determined that the proper state is not obtained even after the predetermined time elapses (NO in step S508), the control unit 21 returns to step S501.

When it is determined that a lesion is detected (YES in step S501), the control unit 21 shifts the mode to a mode in which the guide frame 75 is not displayed as described with reference to FIG. 9 or 10 (step S521). The control unit 21 waits until receiving an instruction to resume the operation in the mode for displaying the guide frame 75 (step S522). After receiving the instruction, the control unit 21 returns to step S501 and resumes the operation of the mode for displaying the guide frame 75.

Figure 18:
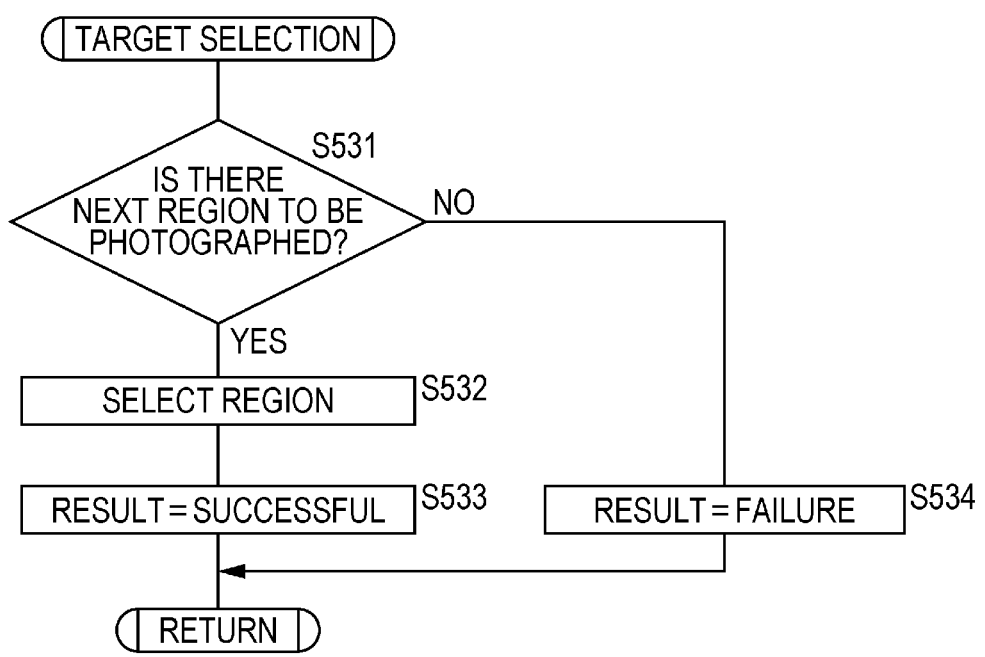
FIG. 18 is a flowchart for explaining a processing flow of a subroutine of a target selection.

FIG. 18 is a flowchart for explaining a processing flow of a subroutine of target selection. The subroutine of the target selection is a subroutine of selecting the region to be photographed for displaying the guide frame 75 from the region to be photographed output from the first learning model 61.

The control unit 21 determines whether a next region to be photographed conforming to a predetermined photographing sequence is included in the region to be photographed output from the first learning model 61 (step S531). When determining that the region to be photographed is included (YES in step S531), the control unit 21 selects the region to be photographed as the display target of the guide frame 75 (step S532). The control unit 21 determines that the processing result of the subroutine of target selection is success (step S533).

When determining that the region to be photographed is not included (NO in step S531), the control unit 21 determines that the processing result of the subroutine of target selection is failure (step S534).

Figure 19:
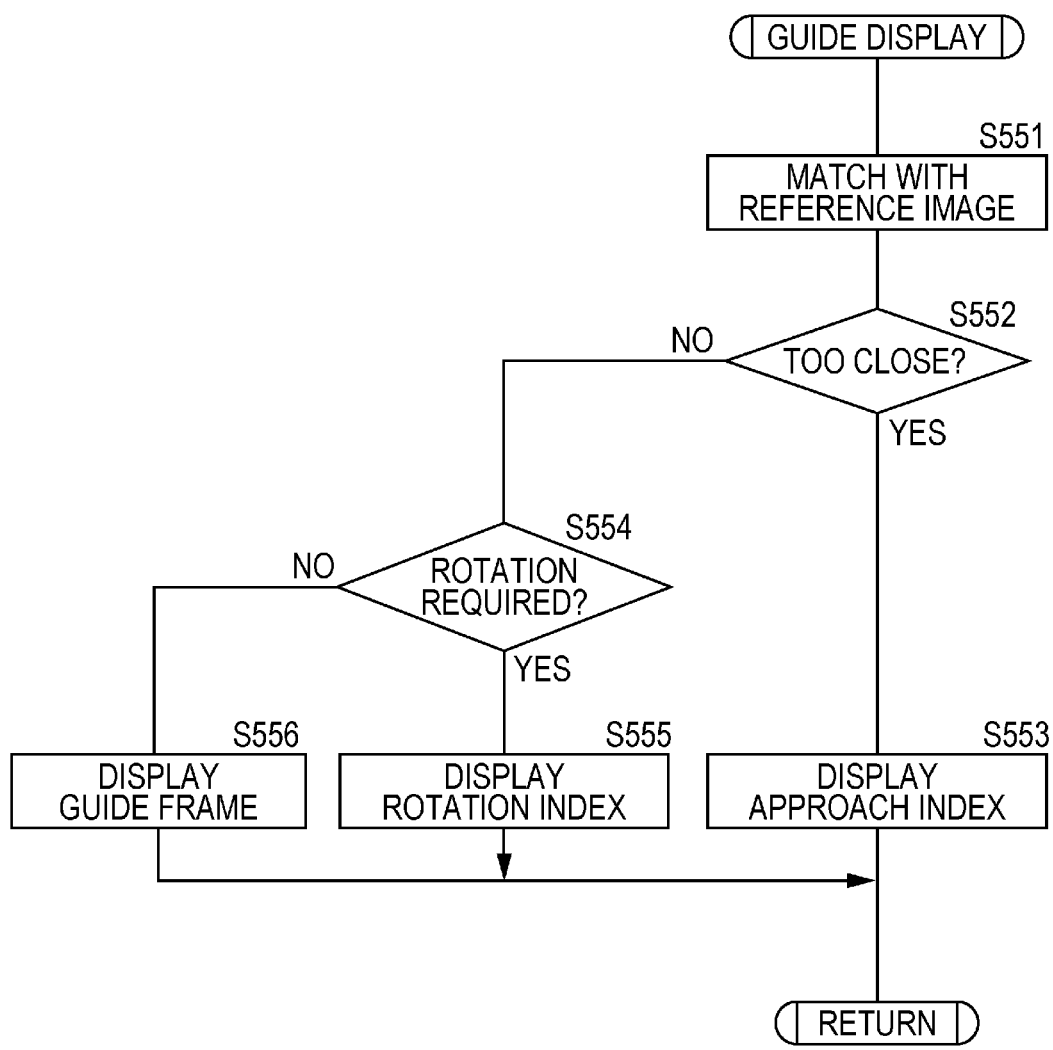
FIG. 19 is a flowchart for explaining a processing flow of a subroutine of a guide display.

FIG. 19 is a flowchart for explaining a processing flow of a subroutine of the guide display. The subroutine of the guide display is a subroutine that displays the guide frame 75 superimposed on the endoscope image 49.

The control unit 21 matches the endoscope image 49 captured in real time with the reference image acquired from the reference image DB 66, and extracts a portion corresponding to the reference image in the endoscope image 49 (step S551).

The control unit 21 determines whether the region to be photographed is too close to the distal end portion 313 (step S552). For example, in a case where the entire endoscope image 49 corresponds to a portion of the reference image, that is, in a case where the reference image is placed beyond the endoscope image 49, the control unit 21 determines that the region to be photographed is too close to the distal end portion 313.

When it is determined that it is too close (YES in step S552), the control unit 21 superimposes the approach index 751 on the endoscope image 49 as described with reference to FIG. 9 and displays it in the endoscope image field 73 (step S553). When it is determined that it is not too close (NO in step S552), the control unit 21 determines whether rotation of the insertion portion 31 is necessary (step S554). For example, in a case where the edge of the matched reference image is rotated with respect to the endoscope image 49, the control unit 21 determines that rotation is necessary.

When determining that the rotation is necessary (YES in step S554), the control unit 21 superimposes the rotation index 752 on the endoscope image 49 as described with reference to FIG. 11 and displays it in the endoscope image field 73 (step S555). When it is determined that the rotation is unnecessary (NO in step S554), the control unit 21 superimposes the guide frame 75 on the endoscope image 49 and displays it in the endoscope image field 73 (step S556). After that, the control unit 21 ends the process.

In step S556, the control unit 21 uses the edge of the range matched with the reference image in step S551 for the guide frame 75.

In step S556, the control unit 21 may change the color, thickness, or line type of the guide frame 75 based on the probability acquired from the first learning model 61. The user can determine the degree to which the guide frame 75 can be trusted.

When determining that it is not too close (NO in step S552), the control unit 21 may proceed to step S556 without determining whether the rotation is necessary. In this case, for example, as described with reference to FIG. 10, the rotation of the endoscope image 49 and the reference image is expressed by the guide frame 75. That is, guide frame 75 also serves as the rotation index 752.

When the dimension of the detection frame 653 acquired from the first learning model 61 is smaller than the predetermined dimension, the control unit 21 may use the detection frame 653 as the guide frame 75 instead of executing the subroutine of the guide display. When the distal end portion 313 is far from the observation target region and the guide frame 75 is displayed to be small on the screen, the load on the control unit 21 can be reduced by using the detection frame 653.

The user operates the endoscope 30 by referring to the guide frame 75, the approach index 751, and the rotation index 752 displayed with them superimposed on the endoscope image 49 by the subroutine of the guide display, so that the endoscope image 49 having high similarity with the reference image can be photographed. That is, the control unit 21 functions as a guide output unit that displays a guide for increasing the similarity between the endoscope image 49 and the reference image by a subroutine of the guide display.

Figure 20:
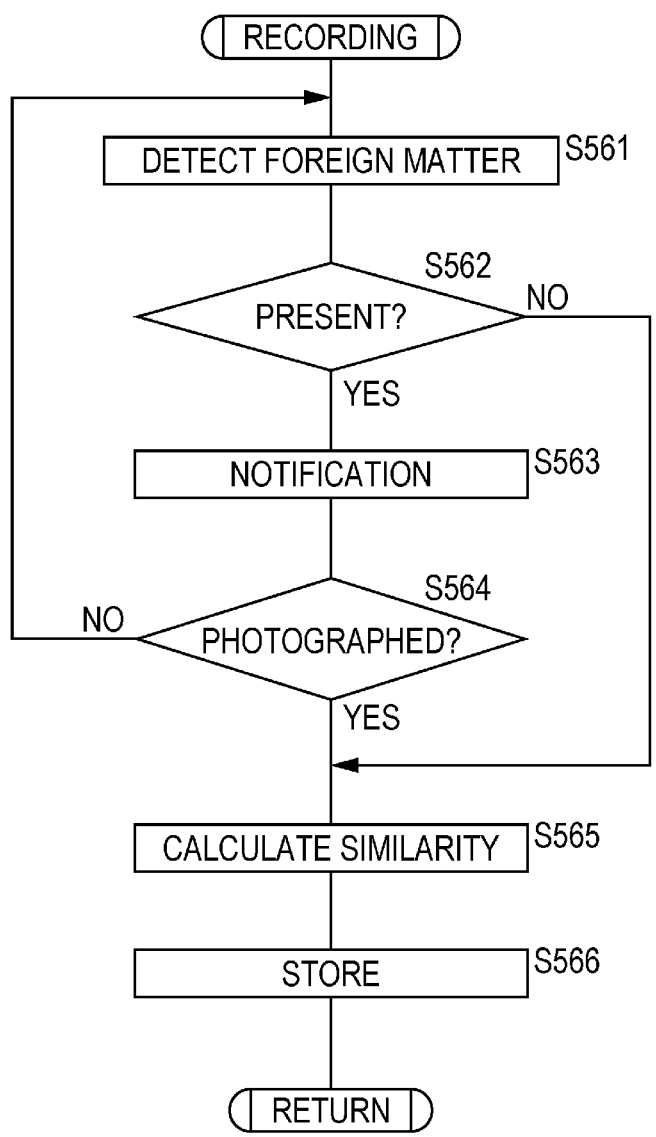
FIG. 20 is a flowchart for explaining a processing flow of a subroutine of a record.

FIG. 20 is a flowchart for explaining a processing flow of a subroutine of a record. The subroutine of a record is a subroutine for recording the endoscope image 49 in the examination DB 67.

The control unit 21 inputs the endoscope image 49 to the second learning model 62 and acquires a region in which the foreign matter such as mucus appears (step S561). The control unit 21 determines whether there is a region in which a probability exceeding the predetermined threshold value is output (step S562). In a case where it is determined that there is a region in which the foreign matter appears with a probability exceeding the threshold value (YES in step S562), the control unit 21 displays the screen described with reference to FIG. 12 and notifies the user of the screen (step S563).

The user who has confirmed the notification removes the foreign matter using the sub water supply function, water supply from the channel, or the like. When it is determined that the image cannot be removed or the image does not need to be removed, the user presses the image capturing button to instruct image capturing.

The control unit 21 determines whether the photographing instruction has been received (step S564). When it is determined that the photographing instruction has not been received (NO in step S564), the control unit 21 returns to step S561.

When it is determined that there is no region in which the foreign matter appears with a probability exceeding the threshold value (NO in step S562), or when it is determined that the photographing instruction is received (YES in step S564), the control unit 21 displays the photograph-in-progress index 761 described using FIG. 13 to notify the user that the endoscope image 49 is to be photographed. The control unit 21 may output sound from the speaker 25 to make notification to the user. The user stops the distal end portion 313 to prevent image blurring. The control unit 21 calculates similarity between the endoscope image 49 and the reference image (step S565).

The control unit 21 stores the endoscope image 49 in the examination DB 67 (step S566). Specifically, the control unit 21 creates a new record in the examination DB 67. The control unit 21 records the doctor ID, the medical examinee ID, and the date in the doctor ID field, the medical examinee ID field, and the date field, respectively. The control unit 21 records numbers in the number field by a serial number. The control unit 21 records the name of the region to be photographed in the region name field. The control unit 21 records the similarity calculated in step S565 in the similarity field. The control unit 21 records the endoscope image 49 in the image field.

The control unit 21 displays in the progress display field 71 that photographing of one region to be photographed is finished. For example, when using the screen described with reference to FIG. 7, the control unit 21 creates a thumbnail of the image recorded in the examination DB 67 and displays the thumbnail in the progress display field 71. When using the screen described with reference to FIG. 8, the control unit 21 displays a check mark in a check box corresponding to the image recorded in the examination DB 67. After that, the control unit 21 ends the process.

In a case where the release operation for acquiring a still image is not performed in step S563, and the endoscope image 49 input to the second learning model 62 is recorded in the examination DB 67 in step S561, the similarity may be calculated simultaneously with the foreign matter detection in step S561, and step S565 may be omitted.

Note that, in a case where the mode is shifted to a mode in which the guide frame 75 is not displayed in step S521 of the program described with reference to FIG. 17, or in a case where the user presses the image capturing button at timing other than step S566, the control unit 21 records the endoscope image 49 in the examination DB 67 as in step S564. In such a case, the control unit 21 records "-" in the region name field and the similarity field.

According to the present embodiment, it is possible to provide the endoscope system 10 that records the endoscope image 49 for the same portion as the reference image defined in the guidelines with the same magnification and layout. The endoscope system 10 of the present embodiment can assist prevention of overlooking in endoscopic examination and improvement of efficiency of double check.

According to the present embodiment, since the guide frame 75 is displayed in accordance with the photographing sequence defined in the guidelines, it is possible to provide the endoscope system 10 that assists photographing in the order according to the guidelines. It is possible to shorten the time required for endoscopic examination by habituating photographing in the order according to the guidelines using the endoscope system 10 according to the present embodiment.

It is possible to provide the endoscope system 10 that does not hinder the work of the doctor by stopping the display of the guide frame 75 in a case where the doctor finds a lesion and starts detailed observation such as special light observation.

It is possible to provide the endoscope system 10 that prevents automatic photographing of the endoscope image 49 in which the foreign matter that hinders diagnosis appears by making notification to the user without capturing an image in a case where the foreign matter such as mucus is detected in the endoscope image 49. Even in a case where the foreign matter is detected, when the user presses the image capturing button, the endoscope image 49 is photographed, so that it is possible to provide the endoscope system 10 that operates in deference to the determination of the doctor.

Second Embodiment

The present embodiment relates to an endoscope system 10 that displays a plurality of guide frames 75 and an endoscope image 49 with the frames superimposed in the image. Descriptions regarding common portions with the first embodiment will be omitted.

Figure 21:
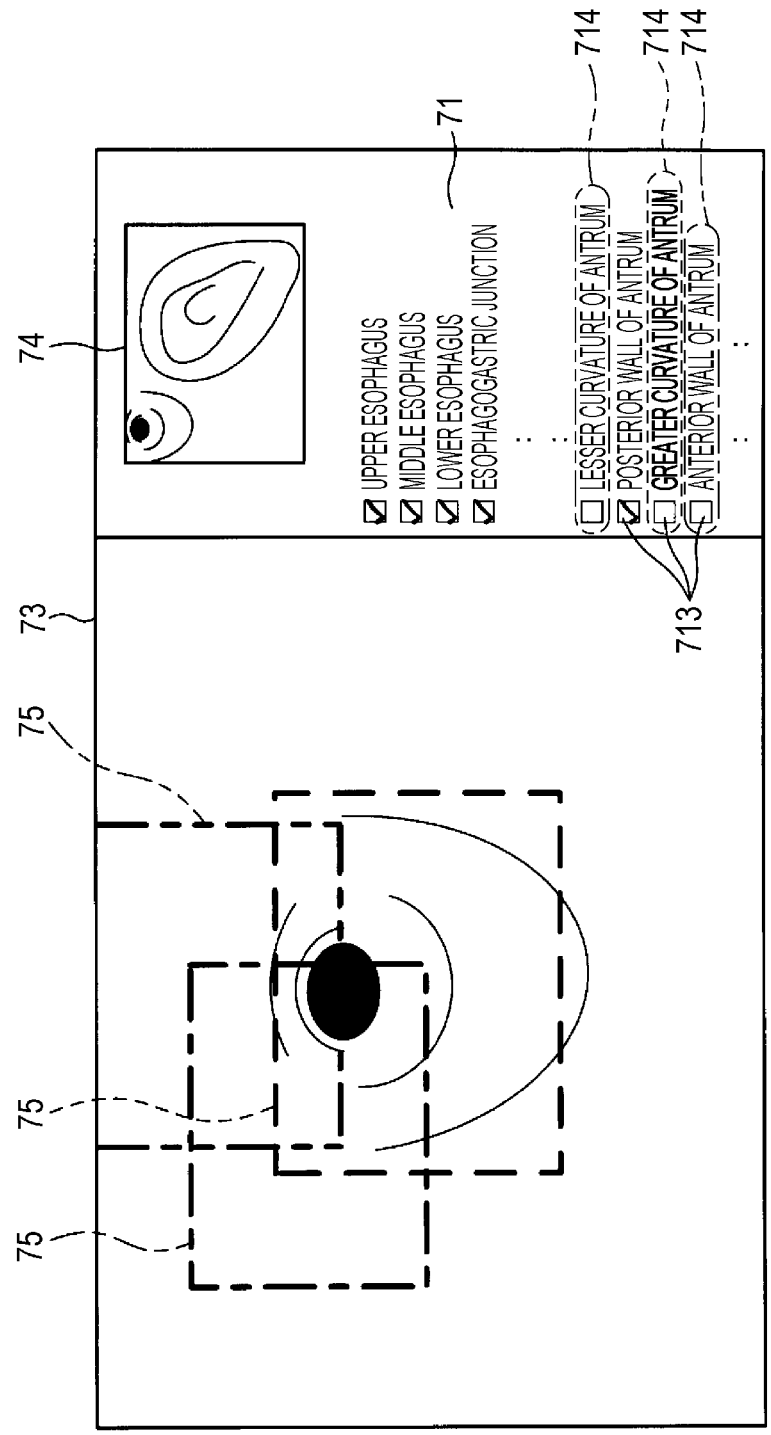
FIG. 21 is an explanatory diagram for explaining a screen display example of a second embodiment.
Figure 22:
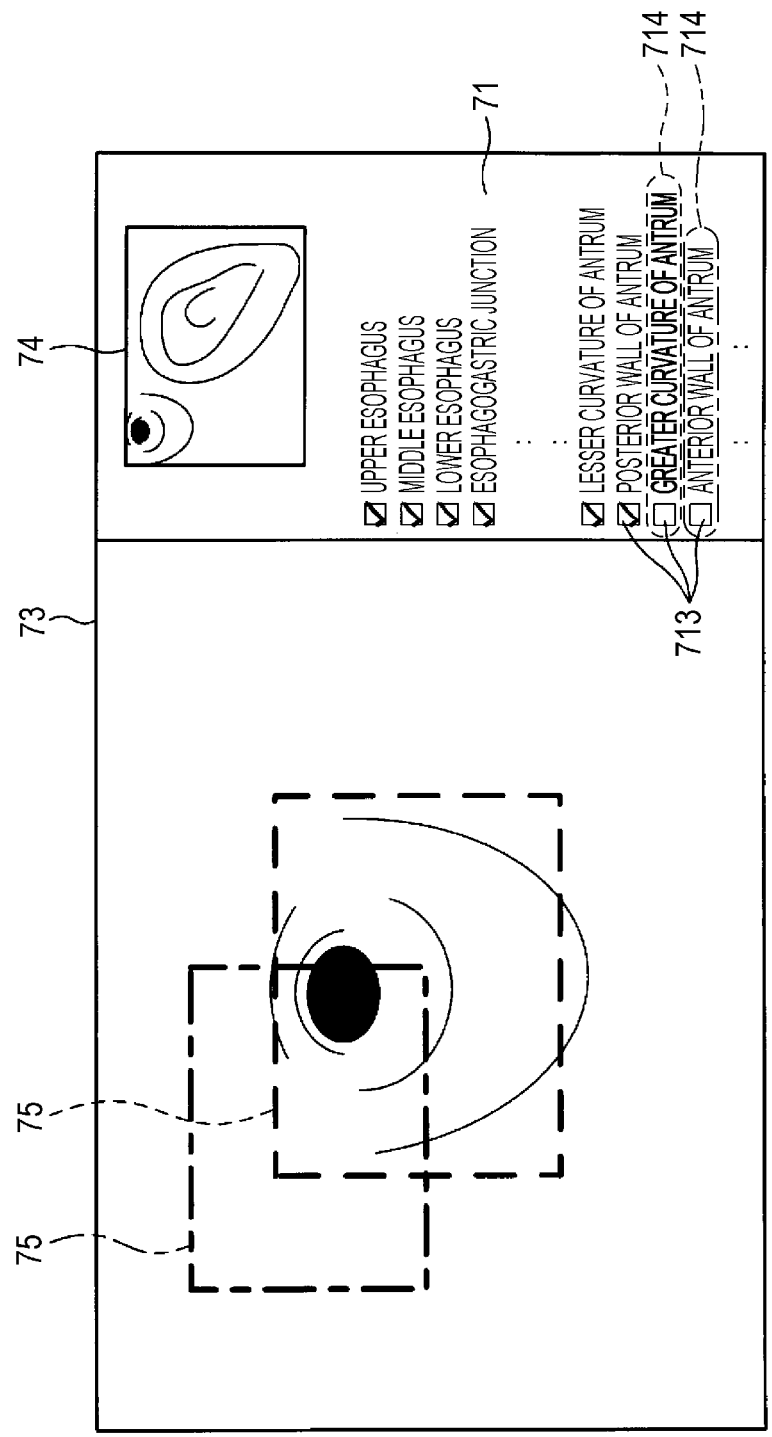
FIG. 22 is an explanatory diagram for explaining a screen display example of the second embodiment.

FIGS. 21 and 22 are explanatory diagrams for explaining screen display examples of the second embodiment. In the screen illustrated in FIG. 21, a plurality of guide frames 75 is displayed in the endoscope image field 73. Each guide frame 75 is indicated by a broken line, a one-dot chain line, and a two-dot chain line.

Similarly to the screen described with reference to FIG. 8, the control unit 21 displays a list of the names of the regions to be photographed defined in the guidelines in the progress display field 71. The control unit 21 displays a check box 713 on the left side of each name. A checked check box 713 means that the image has been captured.

The control unit 21 surrounds the names of the regions to be photographed corresponding to the guide frames 75 indicated by the broken line, the one-dot chain line, and the two-dot chain line with the frame indexes 714 indicated by the broken line, the one-dot chain line, and the two-dot chain line, respectively. Note that the association between the guide frame 75 and the region to be photographed may be indicated by, for example, the color of the guide frame 75 and the character color of the region to be photographed or the color of the line surrounding the region to be photographed.

FIG. 22 is an example of a screen displayed by the control unit 21 after photographing of "lesser curvature of antrum" indicated by the guide frame 75 of the two-dot chain line is completed. The control unit 21 displays a check mark in the check box 713 of "lesser curvature of antrum". After the "lesser curvature of antrum" is photographed, the position of the distal end portion 313 is returned to the same position as when the user captures the image of FIG. 21.

The control unit 21 does not display the guide frame 75 and the frame index 714 corresponding to the photographed "lesser curvature of antrum". The user viewing the screen illustrated in FIG. 22 operates the endoscope 30 so as to photograph the "greater curvature of antrum" or the "anterior wall of antrum" whose guide frame 75 is displayed.

Figure 23:
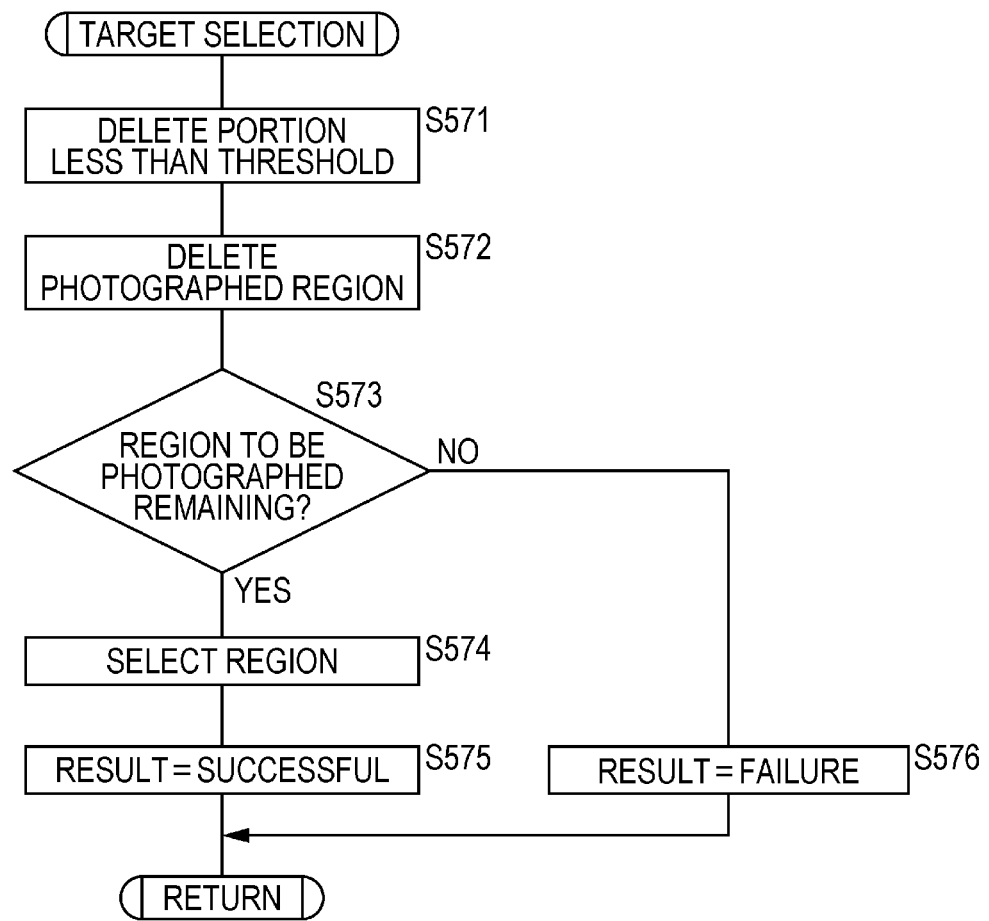
FIG. 23 is a flowchart for explaining a processing flow of the subroutine of the target selection of the second embodiment.

FIG. 23 is a flowchart for explaining a processing flow of a subroutine of target selection of the second embodiment. The subroutine described with reference to FIG. 23 is a subroutine used instead of the subroutine described with reference to FIG. 18.

The control unit 21 deletes a region having a probability less than the predetermined threshold value among the regions to be photographed output from the first learning model 61 (step S571). The control unit 21 deletes the already photographed region from the regions to be photographed remaining in step S571 (step S572).

The control unit 21 determines whether there is a region to be photographed remaining after step S571 (step S573). When it is determined that there is a remaining region to be photographed (YES in step S533), the control unit 21 selects the remaining region to be photographed as a display target of the guide frame 75 (step S574).

The control unit 21 determines that the processing result of the subroutine of target selection is successful (step S575). When it is determined that there is no remaining region to be photographed (NO in step S573), the control unit 21 determines that the processing result of the subroutine of target selection is failure (step S576). After step S575 or step S576 ends, the control unit 21 ends the process.

Figure 24:
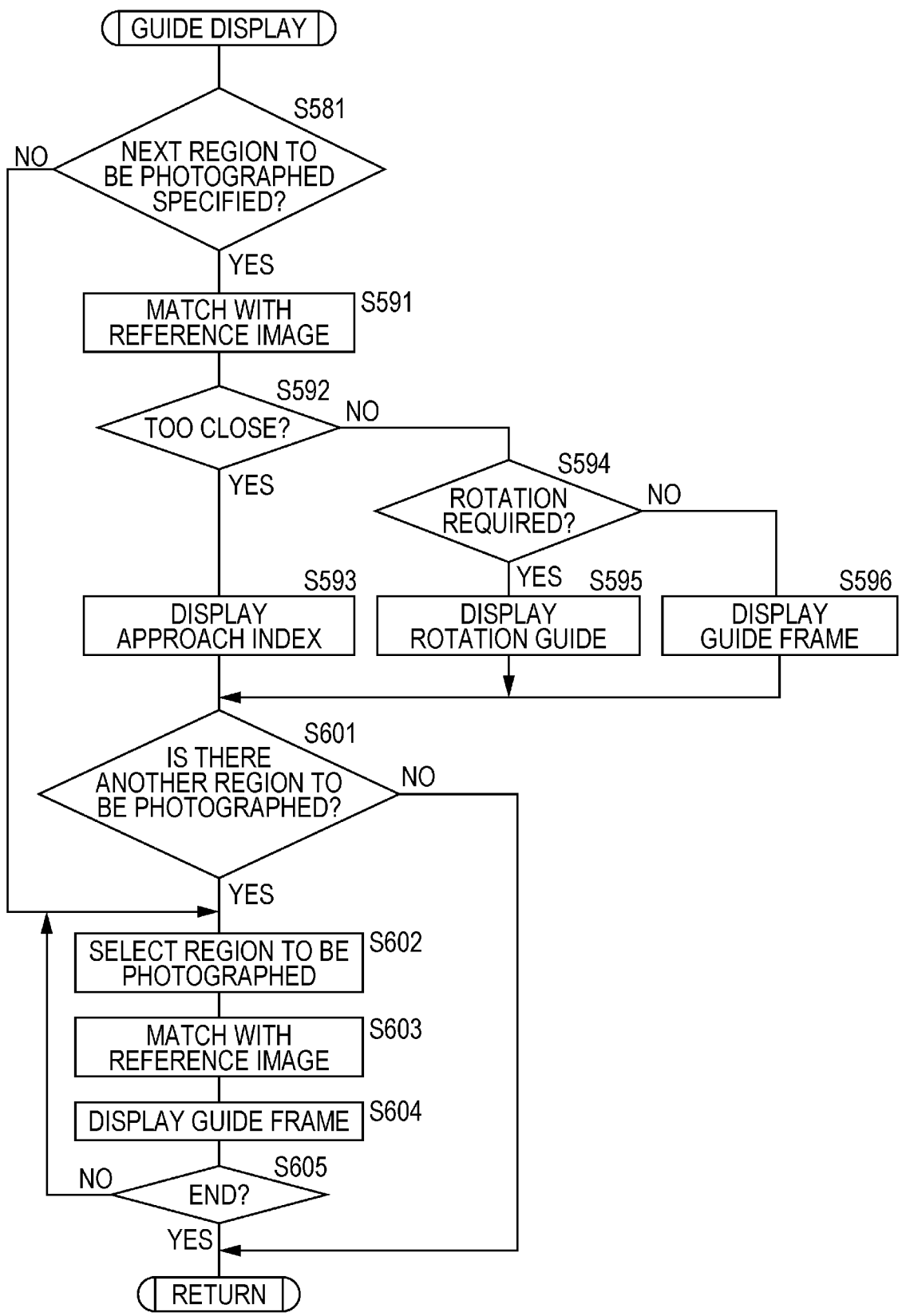
FIG. 24 is a flowchart for explaining a processing flow of a subroutine of a guide display of the second embodiment.

FIG. 24 is a flowchart for explaining a processing flow of a subroutine of the guide display of the second embodiment. The subroutine described with reference to FIG. 24 is a subroutine used instead of the subroutine described with reference to FIG. 19.

The control unit 21 determines whether the user can specify the region to be photographed to be photographed next among the region to be photographed determined to be the display target of the guide frame 75 in the subroutine of target selection (step S581).

Specifically, the control unit 21 determines whether there is a region to be photographed in which the center of the detection frame 653 acquired from the first learning model 61 substantially matches the center of the endoscope image 49 and the dimension of the detection frame 653 is larger than a predetermined value. This is because the region to be photographed satisfying such a condition is the region to be photographed to which the user brings the distal end portion 313 close in front view.

When determining that the region to be photographed can be specified (YES in step S581), the control unit 21 displays the name of the next region to be photographed by surrounding it by the frame index 714. The control unit 21 matches the endoscope image 49 photographed in real time with the reference image of the region to be photographed specified to be photographed next, and extracts a portion corresponding to the reference image in the endoscope image 49 (step S591).

The control unit 21 determines whether the next region to be photographed is too close to the distal end portion 313 (step S592). For example, in a case where the entire endoscope image 49 corresponds to a portion of the reference image, that is, in a case where the reference image is placed beyond the endoscope image 49, the control unit 21 determines that the region to be photographed is too close to the distal end portion 313.

When it is determined that it is too close (YES in step S592), the control unit 21 superimposes the approach index 751 on the endoscope image 49 as described with reference to FIG. 9 and displays it in the endoscope image field 73 (step S593). When it is determined that it is not too close (NO in step S592), the control unit 21 determines whether rotation of the insertion portion 31 is necessary (step S594).

When determining that the rotation is necessary (YES in step S594), the control unit 21 superimposes the rotation index 752 on the endoscope image 49 as described with reference to FIG. 11 and displays it in the endoscope image field 73 (step S595). When it is determined that the rotation is unnecessary (NO in step S594), the control unit 21 superimposes the guide frame 75 corresponding to the target region to be photographed next on the endoscope image 49 and displays it in the endoscope image field 73 (step S596).

After completion of step S593, step S595, or step S596, the control unit 21 determines whether there is a region to be photographed for displaying the guide frame 75 (step S601). When it is determined that there is no region to be photographed (NO in step S601), the control unit 21 ends the process. Note that, in a case where it is determined that there is no region to be photographed, in step S507 after returning from this subroutine to the program described with reference to FIG. 17, there is no guide frame to be tracked, so that it is determined that it is not appropriate state (NO in step S508).

When it is determined that there is the region to be photographed (YES in step S601), or when it is determined that the user cannot specify the region to be photographed to be photographed next (NO in step S581), the control unit 21 selects the region to be photographed for displaying the guide frame 75 next (step S602). The control unit 21 displays the name of the selected region to be photographed by surrounding it by the frame index 714.

The control unit 21 matches the endoscope image 49 captured in real time with the reference image of the region to be photographed selected in step S602, and extracts a portion corresponding to the reference image in the endoscope image 49 (step S603).

The control unit 21 displays the guide frame 75 and the endoscope image 49 with the frame superimposed on the image based on the matching result (step S604). The control unit 21 determines whether display of all guide frames 75 has been finished (step S605). When it is determined that it is not finished (NO in step S605), the control unit 21 returns to step S602. When it is determined that it is finished (YES in step S605), the control unit 21 ends the process.

Note that the guide frame 75 displayed in step S596 may be displayed in a conspicuous form such as a thicker line or a darker color than that of the guide frame 75 displayed in step S604. It is possible to provide the endoscope system 10 in which the user can easily confirm the region to be photographed determined to be photographed next by the control unit 21.

According to the present embodiment, it is possible to provide the endoscope system 10 that assists photographing of a region to be photographed appropriately selected by a user in a case where a plurality of regions to be photographed is included in the same endoscope image 49.

According to the present embodiment, since the guide frames indicating the unphotographed regions to be photographed among the plurality of regions to be photographed included in the endoscope image 49 are displayed at the same time, the user can appropriately perform photographing in the order of easily photographing. Since the guide frame 75 indicating the photographed target region is not displayed, overlapping photographing can be prevented. Note that, in a case where the user wants to photograph the same region to be photographed again, the photographing can be performed by operating the image capturing button.

As described above, it is possible to provide the endoscope system 10 that prevents photographing omission and overlapping photographing. In addition, since the user can perform photographing in an arbitrary order, comfortable operation can be assisted without hindering the operation of the user.

Third Embodiment

The present embodiment relates to the endoscope system 10 that displays a notification when a user performs photographing in an order different from the order of the region to be photographed defined in the guidelines. Description of portions different from those in the second embodiment is omitted.

Figure 25:
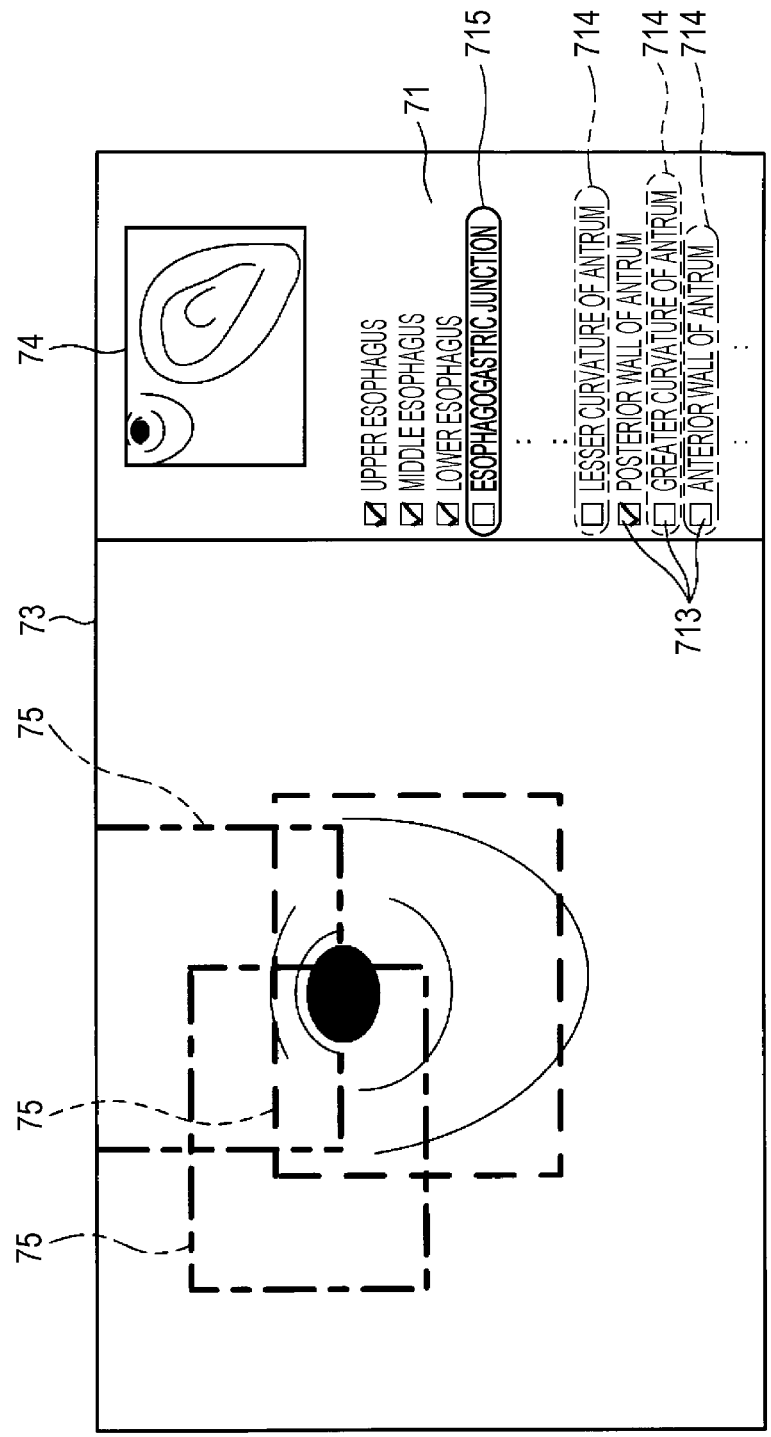
FIG. 25 is an explanatory diagram for explaining a screen display example of a third embodiment.
Figure 26:
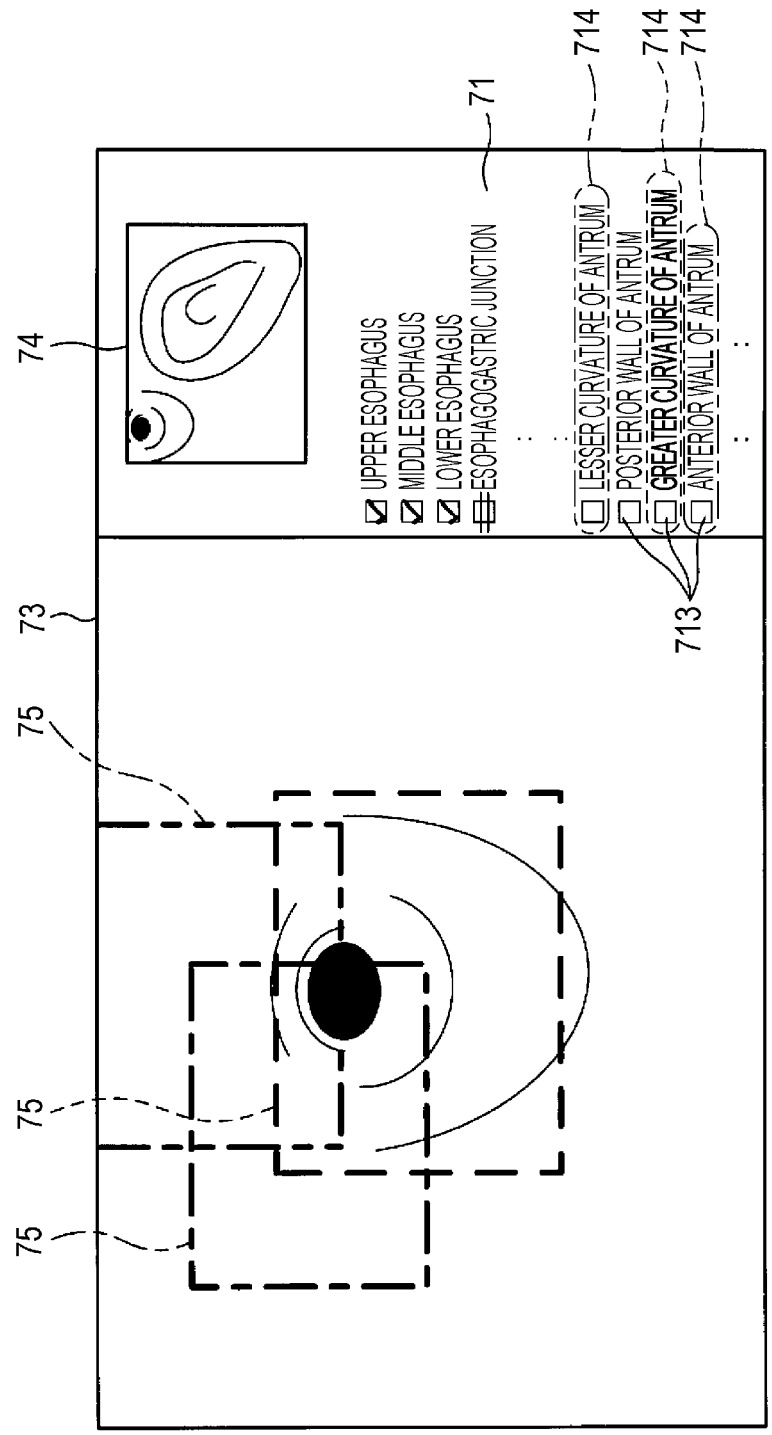
FIG. 26 is an explanatory diagram for explaining a screen display example of the third embodiment.

FIGS. 25 and 26 are explanatory diagrams for explaining the screen display examples of the third embodiment. FIG. 25 illustrates an example of a screen displayed by the control unit 21 when the antrum is observed without photographing the "esophagogastric junction". The control unit 21 surrounds the row of the "esophagogastric junction" with a notification index 715 and notifies that the photographing has not been performed. That is, by displaying the notification index 715, the control unit 21 functions as a second notification output unit that outputs a notification in a case where only the guide frame 75 that does not conform to the predetermined observation sequence defined in the guidelines is displayed.

Note that the control unit 21 may make the row of the "esophagogastric junction" conspicuous by means of blinking or displaying in red, for example. The control unit 21 may further output a voice from speaker 25 to call user's attention. The voice may be a language such as "the esophagogastric junction is not photographed" or a notification sound expressing a sense of caution such as "beep". The control unit 21 also functions as a second notification output unit by these operations.

When the user simply forgets to photograph the esophagogastric junction, the user appropriately operates the endoscope 30 to direct the distal end portion 313 toward the vicinity of the esophagogastric junction. The control unit 21 displays the guide frame 75 corresponding to the esophagogastric junction to assist the user.

When an image corresponding to the reference image cannot be captured for the esophagogastric junction due to the presence of a lesion or the like, the user instructs to cancel the notification by operating the switch button 36, voice input, or the like. FIG. 26 illustrates a state in which the notification related to the esophagogastric junction is canceled. The control unit 21 displays a strike-through line in the check box 713 of the esophagogastric junction and deletes the notification index 715. Thereafter, the user can continue the endoscopic examination without being bothered by the notification.

Figure 27:
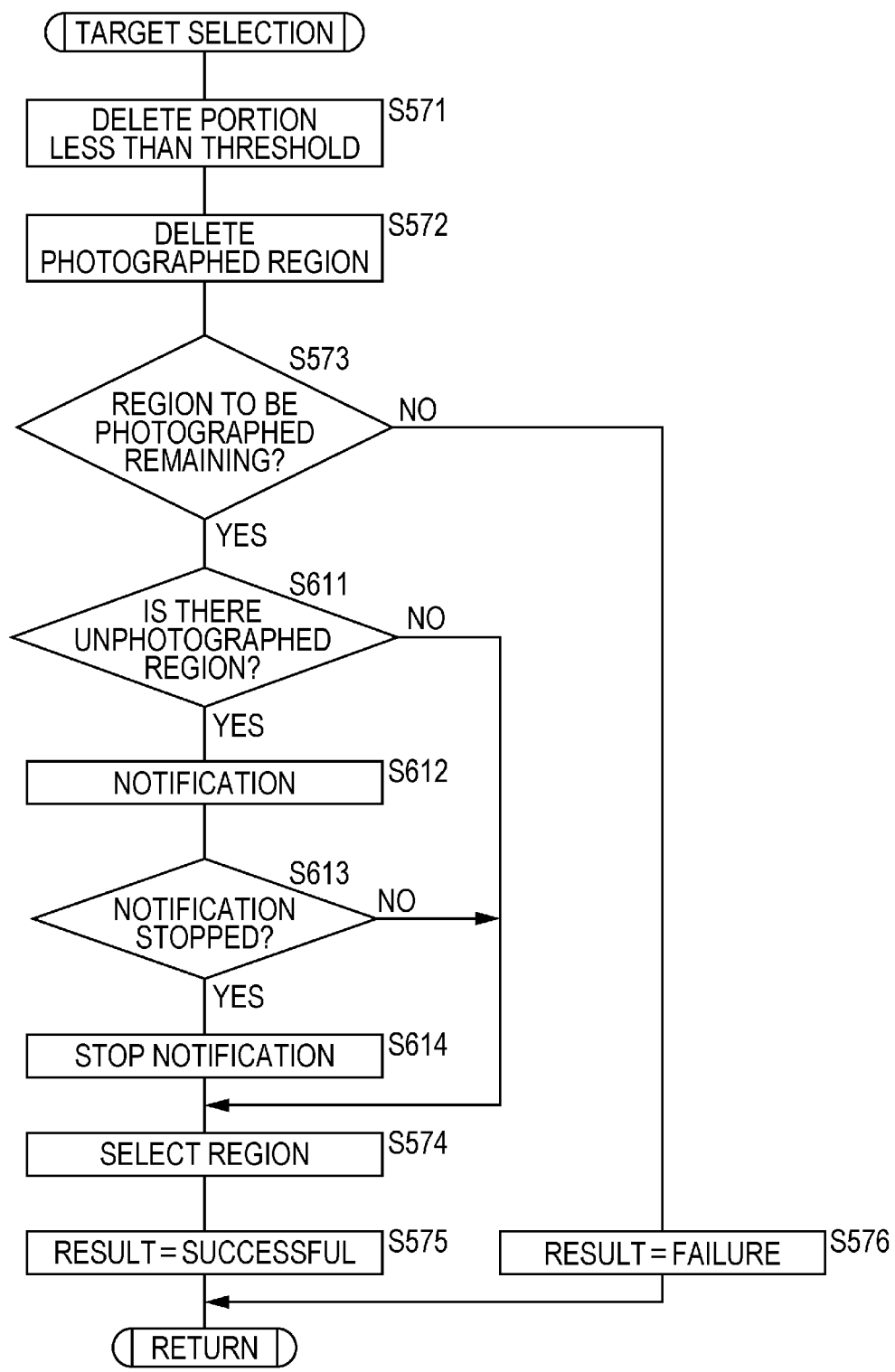
FIG. 27 is a flowchart for explaining a processing flow of a subroutine of the target selection of the third embodiment.

FIG. 27 is a flowchart for explaining a processing flow of a subroutine of the target selection of the third embodiment. The subroutine described with reference to FIG. 27 is a subroutine used instead of the subroutine described with reference to FIG. 23.

The control unit 21 deletes a region having a probability less than the predetermined threshold value among the regions to be photographed output from the first learning model 61 (step S571). The control unit 21 deletes the already photographed region from the regions to be photographed remaining in step S571 (step S572).

The control unit 21 determines whether there is a region to be photographed remaining after step S571 (step S573). When it is determined that there is no remaining region to be photographed (NO in step S573), the control unit 21 determines that the processing result of the subroutine of target selection is failure (step S576).

When it is determined that there is remaining regions to be photographed (YES in step S533), the control unit 21 determines whether there is an unphotographed region set in the guidelines that photographing should be performed before any of the remaining regions to be photographed (step S611). When it is determined that there is an unphotographed region (YES in step S611), the control unit 21 displays the notification index 715 described with reference to FIG. 25 and makes notification to the user.

The control unit 21 determines whether an instruction by the user to stop the notification of the unphotographed region has been received (step S613). When it is determined that the instruction has been received (YES in step S613), the control unit 21 deletes the notification index 715 and stops the notification (step S614). The control unit 21 temporarily stores, in the main storage device 22 or the auxiliary storage device 23, that the instruction to stop the notification has been received, and does not make the notification regarding the unphotographed region in step S612 to be executed in a loop thereafter.

When it is determined that there is no unphotographed region (NO in step S611), when it is determined that an instruction to stop the notification is not received (NO in step S613), or after the end of step S614, the control unit 21 selects all remaining regions to be photographed as display targets of the guide frame 75 (step S574).

The control unit 21 determines that the processing result of the subroutine of target selection is successful (step S575). After step S575 or step S576 ends, the control unit 21 ends the process.

According to the present embodiment, it is possible to provide the endoscope system 10 that attracts the attention of the user in a case where the user photographs the next region to be photographed without photographing the region to be photographed. It is possible to provide the endoscope system 10 that does not trouble the user more than necessary by accepting the stop of the notification in a case where the user intentionally omits photographing of the region to be photographed.

Fourth Embodiment

The present embodiment relates to the endoscope system 10 that displays cautions at the time of photographing Descriptions regarding common portions with the first embodiment will be omitted.

Figure 28:
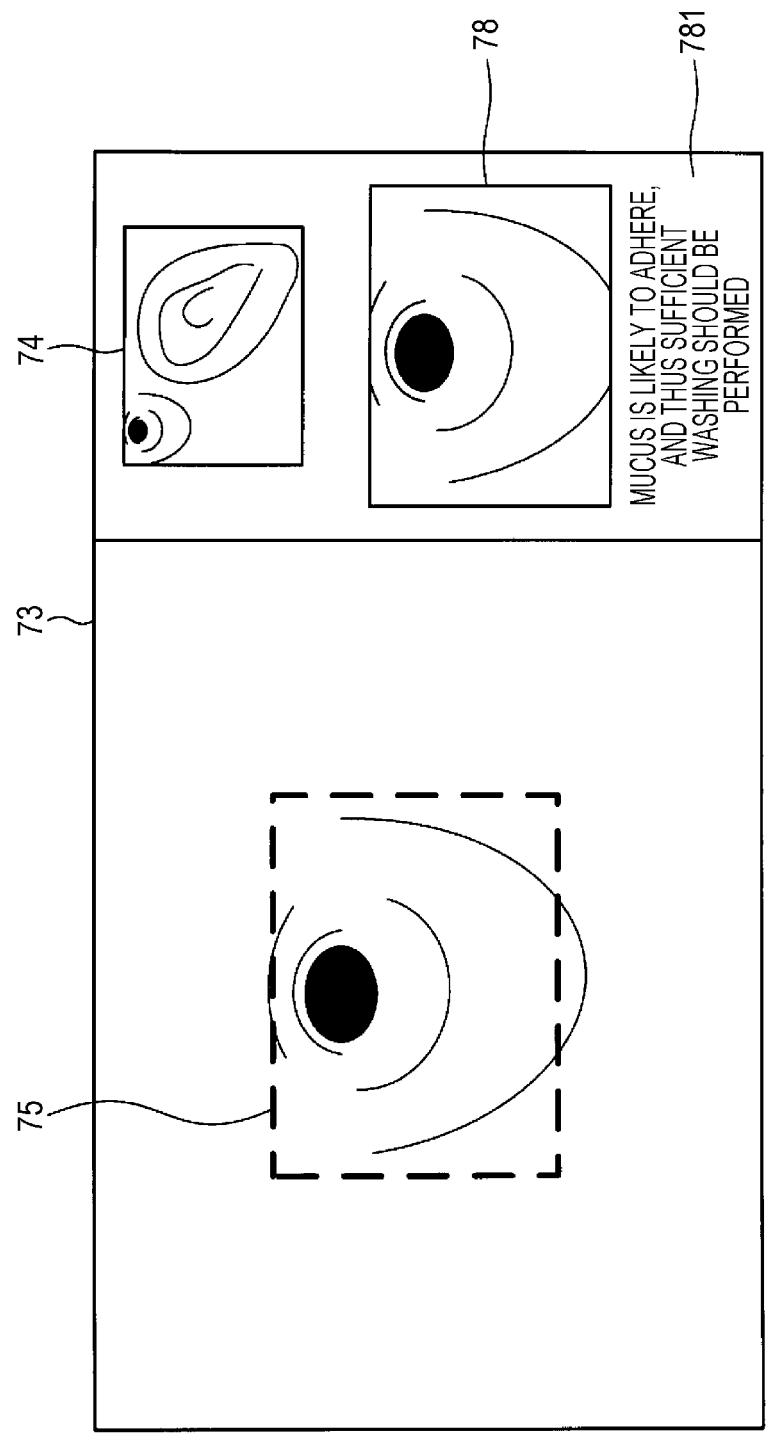
FIG. 28 is an explanatory diagram for explaining a screen display example of a fourth embodiment.

FIG. 28 is an explanatory diagram for explaining a screen display example of the fourth embodiment. In a case where the guide frame 75 is displayed at the center of the endoscope image 49 with a size equal to or larger than a predetermined size, it can be estimated that the user has started preparation for photographing. The control unit 21 displays the reference image corresponding to the guide frame 75 in a reference image field 78, and displays the attention item at the time of photographing the region to be photographed in an attention item field 781 below the reference image field. Note that the attention item is recorded in association with the reference image in the reference image DB 66, for example.

According to the present embodiment, the user can perform cleaning or the like according to the attention item while performing the operation of directing the distal end portion 313 toward the region to be photographed. Therefore, it is possible to provide the endoscope system 10 that assists the user so that an appropriate image can be smoothly captured.

Fifth Embodiment

Figure 29:
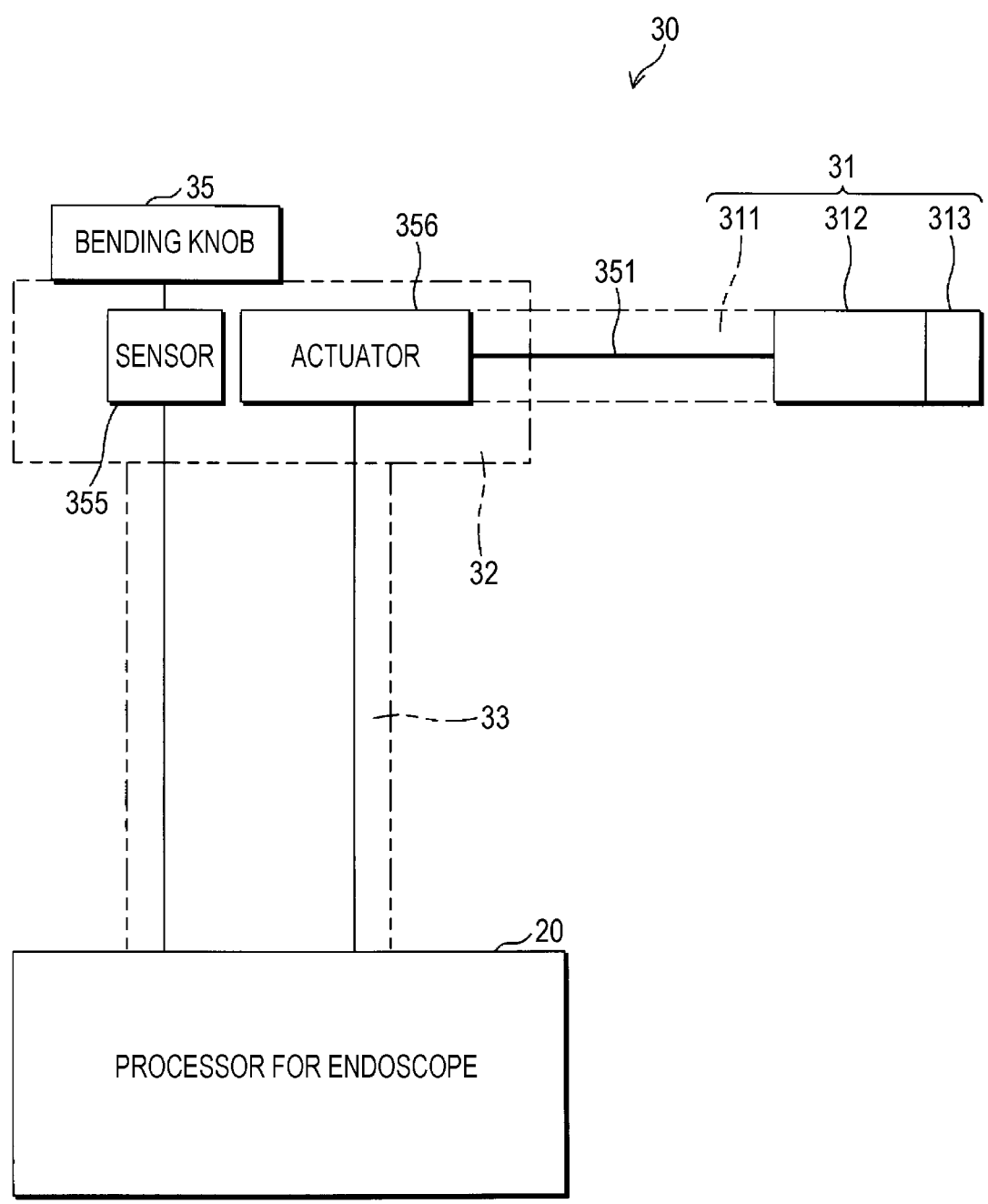
FIG. 29 is an explanatory diagram for explaining the configuration of an endoscope system of a fifth embodiment.

The present embodiment relates to the endoscope system 10 in which the control unit 21 automatically controls the bending section 312 to capture an image close to the reference image. Descriptions regarding common portions with the first embodiment will be omitted. FIG. 29 is an explanatory diagram for explaining the configuration of the endoscope system 10 of the fifth embodiment.

In FIG. 29, a configuration related to the operation of the bending section 312 is schematically described, and description of other portions is omitted. In FIG. 29, one bending knob 35 is schematically illustrated. By having the same configuration in both the U-D (Up-Down) direction and the R-L (Right-Left) direction, it is possible to automatically control so-called four-direction bending.

A sensor 355 that detects an operation amount by a user is attached to the bending knob 35. The sensor 355 is connected to the processor for an endoscope 20. A bending wire 351 that bends the bending section 312 is connected to an actuator 356 provided in the operation unit 32.

When the user operates the bending knob 35, the control unit 21 controls the actuator 356 according to the operation amount detected by the sensor 355. The bending section 312 is bent by pulling the bending wire 351 by the actuator 356. Therefore, the user can perform the bending operation of the bending section 312 by operating the bending knob 35 similarly to the normal endoscope 30.

Figure 30:
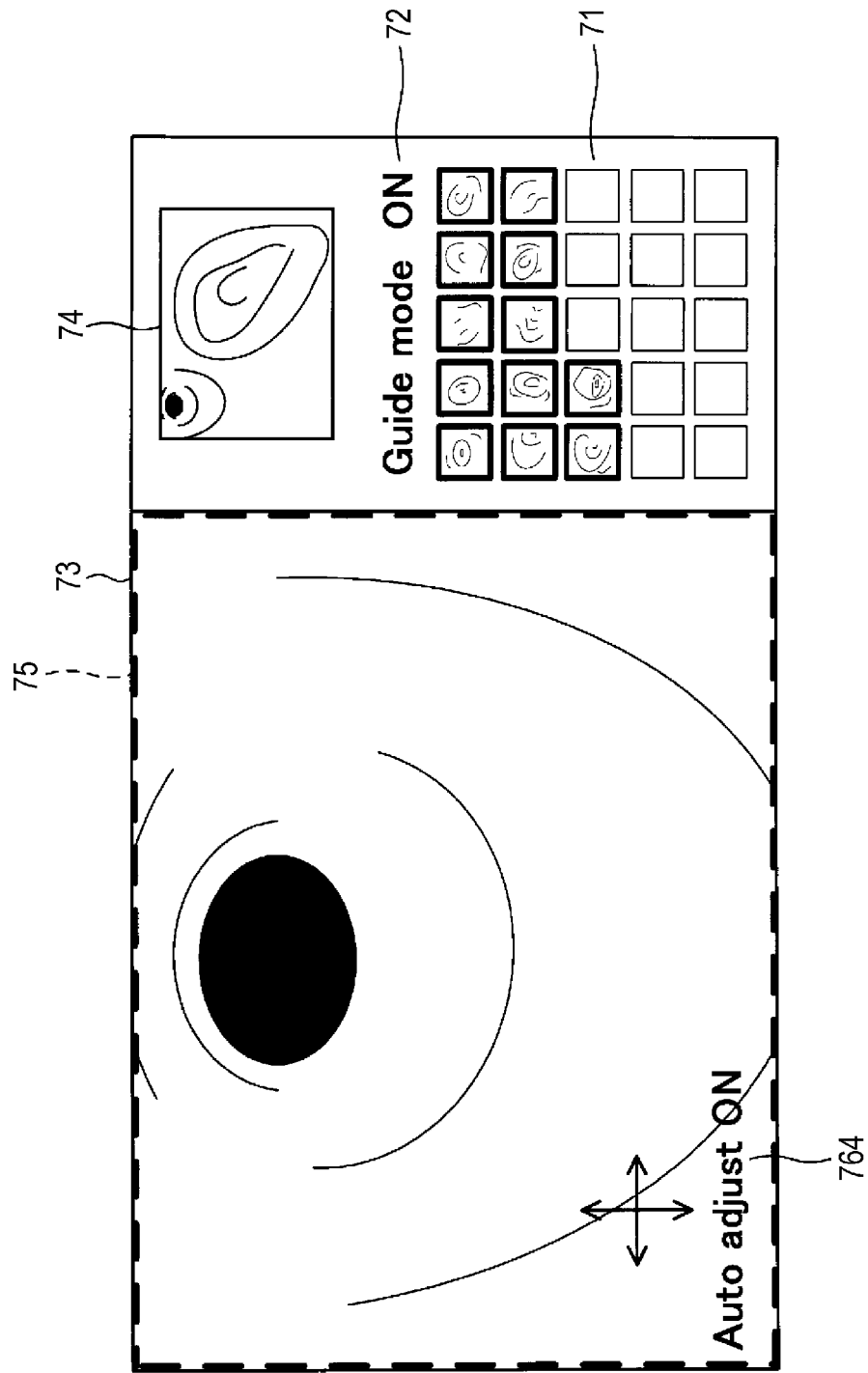
FIG. 30 is an explanatory diagram for explaining a screen display example of the fifth embodiment.

FIG. 30 is an explanatory diagram for explaining a screen display example of the fifth embodiment. In the present embodiment, when the guide frame 75 approaches the edge of the endoscope image 49, the control unit 21 shifts to the automatic control mode and displays an automatic control-in-progress mark 764. That is, by displaying the automatic control-in-progress mark 764, the control unit 21 functions as a third notification output unit that outputs a notification in a case where the endoscope 30 is automatically controlled.

In the automatic control mode, the control unit 21 automatically controls the bending section 312 via the actuator 356 so that the guide frame 75 matches the edge of the endoscope image 49, performs alignment in an appropriate state, and then automatically performs photographing.

Figure 31:
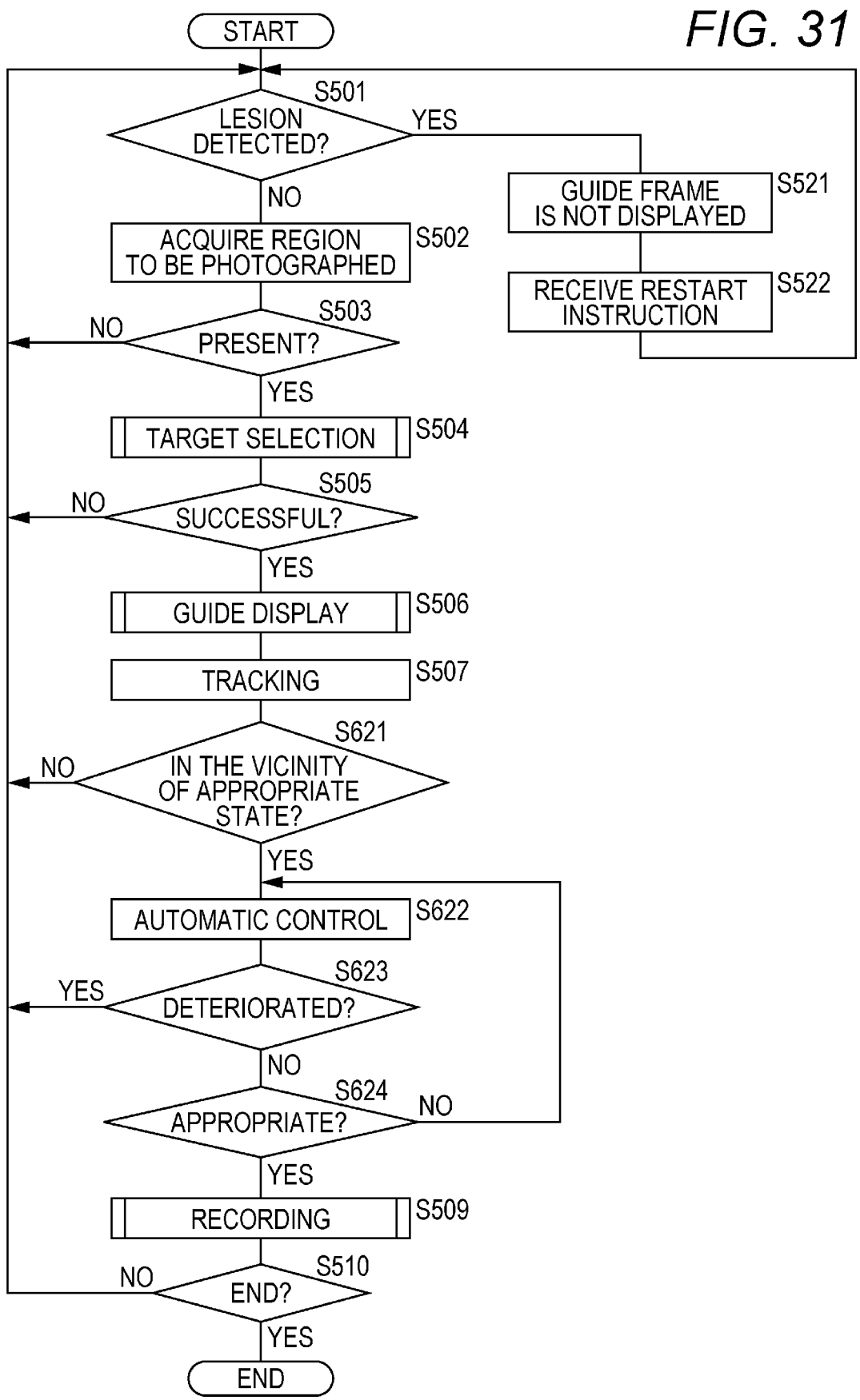
FIG. 31 is a flowchart for explaining a processing flow of a program of the fifth embodiment.

FIG. 31 is a flowchart for explaining a processing flow of the program of the fifth embodiment. Since the processing flow from the start to step S507 is similar to the flowchart described with reference to FIG. 17, the description thereof will be omitted.

The control unit 21 determines whether the endoscope image 49 is in the vicinity of an appropriate state for photographing a region to be photographed (step S621). Specifically, in a case where the edge of the endoscope image 49 and the guide frame 75 being tracked are close to each other, the control unit 21 determines that they are in the vicinity of an appropriate state. In a case where the similarity between the endoscope image 49 and the reference image exceeds a predetermined threshold value, the control unit 21 may determine that they are in the vicinity of the appropriate state.

When it is determined that they are in the vicinity of the appropriate state (YES in step S621), the control unit 21 shifts to the automatic control mode and automatically controls the actuator 356 so that the endoscope image 49 approaches the reference image (step S622).

The control unit 21 determines whether the state of the endoscope image 49 has deteriorated by the automatic control (step S623). Specifically, in a case where the edge of the endoscope image 49 and the guide frame 75 being tracked are away from each other, the control unit 21 determines that the state has deteriorated. The control unit 21 may determine that the state has deteriorated in a case where the similarity between the endoscope image 49 and the reference image has decreased.

When it is determined that the state has deteriorated (YES in step S621), the control unit 21 returns to step S501. When it is determined that the state has not deteriorated (NO in step S621), the control unit 21 determines whether the endoscope image 49 is in an appropriate state for photographing the region to be photographed (step S624). Specifically, in a case where most of the area of the endoscope image 49, for example, 90% or more, is surrounded by the guide frame 75 being tracked, the control unit 21 determines that it is in an appropriate state.

When it is determined that it is not in an appropriate state (NO in step S624), the control unit 21 returns to step S622. When it is determined that it is in an appropriate state (YES in step S624), the control unit 21 activates a subroutine of a record (step S509). Since the subsequent processing is the same as the program described with reference to FIG. 17, description is omitted.

According to the present embodiment, since fine adjustment immediately before photographing is automatically performed, it is possible to provide the endoscope system 10 with less burden on the user. Since the operation other than the fine adjustment is manually performed by the user, it is possible to provide the endoscope system 10 capable of performing the endoscopic examination similarly to the related art.

Note that the endoscope system 10 may be configured such that the control unit 21 can automatically control air/water supply, sub water supply, adjustment of zoom magnification, and the like in addition to the bending section 312. By performing the automatic control, the control unit 21 functions as an automatic control unit that operates the endoscope 30 so as to increase the similarity between the endoscope image 49 and the reference image.

Sixth Embodiment

The present embodiment relates to an endoscope system 10 having a training function of an endoscopic examination manipulation according to the guidelines. Descriptions regarding common portions with the first embodiment will be omitted.

FIG. 32 is an explanatory diagram for explaining a screen display example of the sixth embodiment. After completion of the endoscopic examination according to the guidelines, the control unit 21 displays the screen illustrated in FIG. 32. A score field 79 is displayed on the screen illustrated in FIG. 32. In the score field 79, the number of images captured according to the guidelines in a series of endoscopic examinations and representative values of similarity such as an average point, a highest point, and a lowest point of similarity are displayed. The control unit 21 may display the required time and the like.

In a case where the examination of one medical examinee ends and the endoscope 30 is removed from the medical examinee, the control unit 21 calculates the score based on the examination DB 67 and displays the screen illustrated in FIG. 32. It can be seen that the higher the similarity is, the more appropriately the endoscope image 49 according to the guidelines can be captured, and the higher the proficiency level is. That is, the control unit 21 functions as an evaluation display unit that displays the evaluation of the manipulation by the user based on the similarity by outputting the screen illustrated in FIG. 32.

The control unit 21 may display the transition of the score in a predetermined period such as one month or one year as a graph. The user can check the degree of improvement of the endoscopic examination by leveling the difficulty level of insertion for each subject by the transition of the score.

The control unit 21 may display the comparison with the score of another user by, for example, a deviation value, a graph, or the like. The user can grasp the relative level of his or her manipulation.

According to the present embodiment, by displaying the score of the endoscopic examination manipulation, it is possible to provide the endoscope system 10 that assists improvement of the manipulation by the user, that is, training of the user. The user can use the endoscope system 10 of the present embodiment as a training device that performs training of a manipulation of endoscopic examination.

Seventh Embodiment

The present embodiment relates to an endoscope system 10 used for a follow-up observation of a patient. Descriptions regarding common portions with the first embodiment will be omitted.

For example, after the endoscopic treatment is performed, the same place is periodically observed, and a follow-up observation is performed to confirm progress of healing, presence or absence of recurrence, or the like. In the follow-up observation, it is desirable to photograph an image with the same magnification and layout as possible every time.

FIG. 33 is an explanatory diagram for explaining a record layout of the follow-up observation DB. The follow-up observation DB includes a medical examinee ID field, a photographing date field, and an image field.

In the medical examinee ID field, the medical examinee ID is recorded. In the photographing date field, a photographing date is recorded. In the image field, a file of still images is recorded.

The follow-up observation DB has one record for each follow-up observation. The follow-up observation DB is stored in the auxiliary storage device 23 or an external mass storage device connected to the processor for an endoscope 20.

Figure 34:
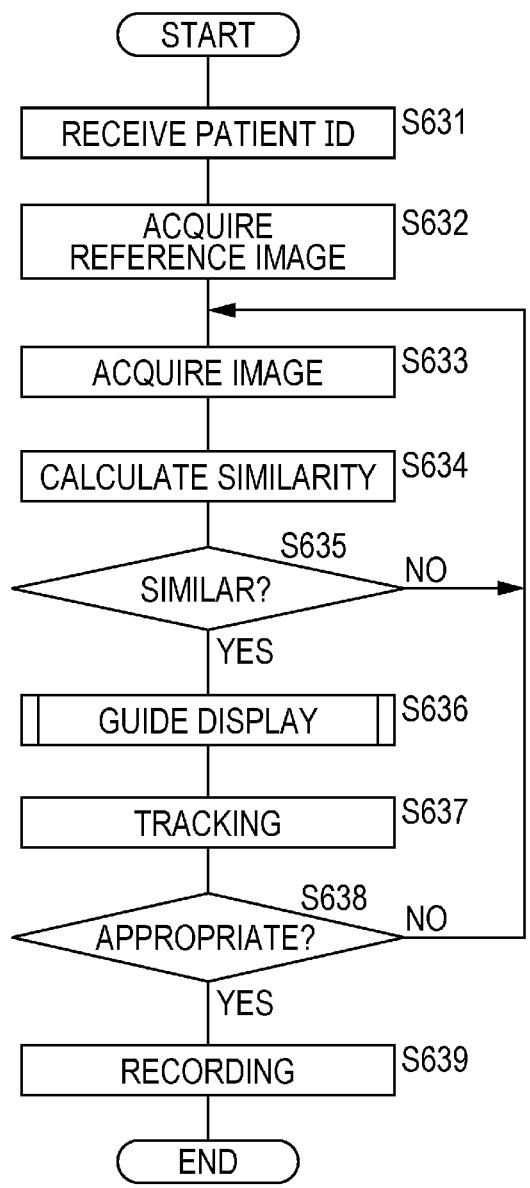
FIG. 34 is a flowchart for explaining a processing flow of a program of the seventh embodiment.

FIG. 34 is a flowchart for explaining a processing flow of the program of the seventh embodiment. The control unit 21 receives an input of the medical examinee ID (step S631). The control unit 21 searches the follow-up observation DB using the medical examinee ID as a key, extracts a record to acquire a reference image from the image field (step S632). The reference image is, for example, an image at the time of the previous follow-up observation. An image at the time of the first follow-up observation may be used as the reference image.

The control unit 21 acquires the real-time endoscope image 49 (step S633). The control unit 21 calculates similarity between the endoscope image 49 and the reference image (step S634). The control unit 21 determines whether the calculated similarity is higher than a predetermined threshold value (step S635).

When it is determined that the similarity is higher than the predetermined threshold value (YES in step S635), the control unit 21 activates a subroutine of the guide display (step S636). The subroutine of the guide display is the same subroutine as the subroutine described with reference to FIG. 19.

The control unit 21 performs tracking of changing the display of the guide frame 75 in accordance with the change in the endoscope image 49 (step S637). The control unit 21 determines whether the endoscope image 49 is in an appropriate state for photographing an image of the follow-up observation (step S538). Specifically, in a case where most of the area of the endoscope image 49, for example, 90% or more, is surrounded by the guide frame 75 being tracked, the control unit 21 determines that it is in an appropriate state.

When it is determined that it is in an appropriate state (YES in step S638), the control unit 21 photographs a new record in the follow-up observation DB and records the endoscope image 49 (step S639). After that, the control unit 21 ends the process.

When it is determined that the similarity is lower than the predetermined threshold value (NO in step S635) or when it is determined that it is not in an appropriate state (NO in step S638), the process returns to step S633.

According to the present embodiment, it is possible to provide the endoscope system 10 that repeatedly records the follow-up observation image with the same image and layout. The doctor can accurately determine the progress such as the state of cure or the state of recurrence.

Eighth Embodiment

Figure 35:
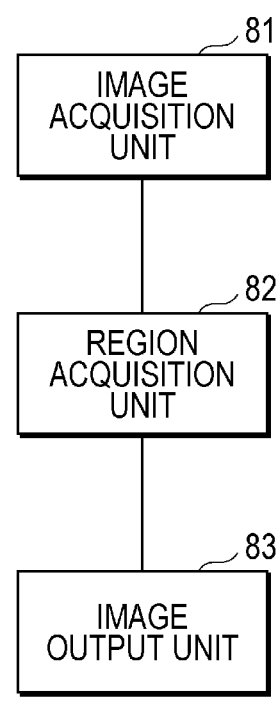
FIG. 35 is a functional block diagram of a processor for an endoscope of an eighth embodiment.

FIG. 35 is a functional block diagram of the processor for an endoscope 20 of the eighth embodiment. The processor for an endoscope 20 includes an image acquisition unit 81, a region acquisition unit 82, and an image output unit 83. The image acquisition unit 81 acquires the endoscope image 49. The region acquisition unit 82 inputs the endoscope image 49 acquired by the image acquisition unit 81 to the first learning model 61 that outputs a target region corresponding to a predetermined region to be photographed when the endoscope image 49 is input, and acquires the target region. The image output unit 83 superimposes the endoscope image 49 acquired by the image acquisition unit 81 and the index 75 indicating the target region acquired by the region acquisition unit 82 to output them.

Ninth Embodiment

Figure 36:
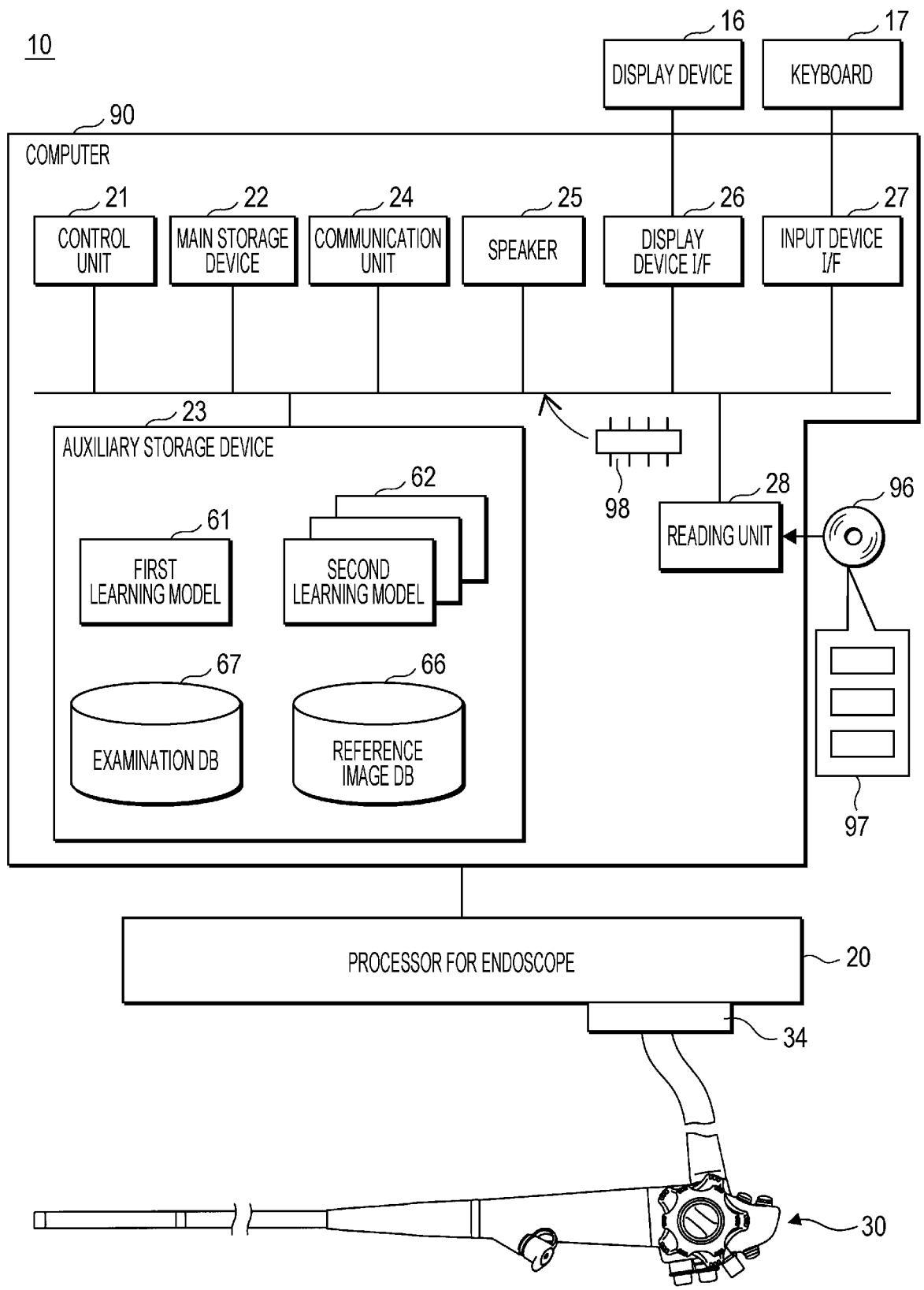
FIG. 36 is an explanatory diagram for explaining the configuration of an endoscope system of a ninth embodiment.

The present embodiment relates to a mode for realizing the endoscope system 10 of the present embodiment by operating the general-purpose computer 90 and the program 97 in combination. FIG. 36 is an explanatory diagram for explaining the configuration of the endoscope system 10 of the ninth embodiment. Descriptions regarding common portions with the first embodiment will be omitted.

The endoscope system 10 according to the present embodiment includes an endoscope 30, a processor for an endoscope, and a computer 90. The computer 90 includes the control unit 21, the main storage device 22, the auxiliary storage device 23, the communication unit 24, the speaker 25, the display device I/F 26, the input device I/F 27, the reading unit 28, and the bus. The computer 90 is an information device such as a general-purpose personal computer, a tablet, or a server computer.

The computer 90 is connected to the processor for an endoscope 20 in a wired or wireless manner to acquire the endoscope image 49 from the processor for an endoscope 20 in real time.

A program 97 is recorded in a portable recording medium 96. The control unit 21 reads the program 97 via the reading unit 28 and stores it in the auxiliary storage device 23. Further, the control unit 21 may read the program 97 stored in a semiconductor memory 98 such as a flash memory mounted in the computer 90. Further, the control unit 21 may download the program 97 from the communication unit 24 and another server computer (not illustrated) connected via a network (not illustrated), and store the program 97 in the auxiliary storage device 23.

The program 97 is installed as a control program for the computer 90 and is loaded and executed in the main storage device 22. As a result, the computer 90 functions as a control device of the endoscope system 10.

Technical features (constitutional requirements) described in the respective embodiments can be combined with each other, and new technical features can be formed with the combination.

The embodiments herein are disclosed for purposes of illustration in all respects and not limitation. The scope of the present invention is defined not by the above-described meaning but by claims, and intends to include all modifications within meaning and a scope equal to claims.

REFERENCE SIGNS LIST 10 endoscope system
16 display device
17 keyboard
20 processor for an endoscope
21 control unit
22 main storage device
23 auxiliary storage device
24 communication unit
25 speaker
26 display device I/F
27 input device I/F
28 reading unit
29 endoscope connection unit
30 endoscope
31 insertion portion
311 soft portion
312 bending section
313 distal end portion
32 operation unit
321 air/water supply button
322 suction button
33 universal cord
34 connector unit
35 bending knob
351 bending wire
355 sensor
356 actuator
36 switch button
37 channel inlet
371 forceps plug
49 endoscope image
61 first learning model
62 second learning model
651 region candidate extraction unit
652 classification unit
653 detection frame
66 reference image DB
67 examination DB
71 progress display field
713 check box
714 frame index
715 notification index
72 state display field
73 endoscope image field
74 past image field
75 guide frame (index)
751 approach index
752 rotation index
753 lesion frame
754 accretion frame
761 photograph-in-progress index
762 accretion mark
763 detection notification field
764 automatic control-in-progress mark
77 guide-in-progress mark
78 reference image field
781 attention item field
79 score field
81 image acquisition unit
82 region acquisition unit
83 image output unit
90 computer
96 portable recording medium
97 program
98 semiconductor memory

The invention claimed is:

1. A processor for an endoscope comprising:
an image sensor that acquires an endoscope image;
a processor that inputs the endoscope image acquired by the image sensor to a first learning model that outputs a target region corresponding to a predetermined region to be photographed when the endoscope image is input to acquire the target region; and
a display that displays the endoscope image acquired by the image sensor and an index indicating the target region acquired by the processor with the endoscope image and the index superimposed,
wherein the processor outputs a guide for increasing the similarity between the endoscope image acquired by the image sensor and a reference image associated with a region to be photographed with the guide superimposed on the endoscope image.

2. The processor for an endoscope according to claim 1, wherein the processor records the endoscope image acquired by the image sensor in a case where it is determined that the similarity between the endoscope image acquired by the image sensor and a reference image associated with a region to be photographed is higher than a predetermined value.

3. The processor for an endoscope according to claim 2, wherein the processor outputs a notification when the processor records the endoscope image.

4. The processor for an endoscope according to claim 3, wherein the processor outputs a notification according to the similarity between the recorded endoscope image and the reference image.

5. The processor for an endoscope according to claim 2, wherein the processor records the endoscope image acquired by the image sensor when receiving an instruction from a user.

6. The processor for an endoscope according to claim 1, wherein
the first learning model outputs a plurality of target regions corresponding to a plurality of respective regions to be photographed when the endoscope image is input, and
the display displays the endoscope image and an index indicating each of the plurality of target regions with the endoscope image and the index superimposed with each other.

7. The processor for an endoscope according to claim 6, wherein the display does not superimpose an index corresponding to a region to be photographed for which a corresponding endoscope image has been recorded.

8. The processor for an endoscope according to claim 1, wherein the processor outputs a notification when the display displays only an index corresponding to a reference image that does not conform to a predetermined observation sequence.

9. The processor for an endoscope according to claim 1, wherein the processor detects that a lesion is being observed, and stops an operation in a case where the processor detects that the lesion is being observed.

10. The processor for an endoscope according to claim 9, wherein the processor determines a restart of an operation of the processor, and when the restart of the operation is determined, the processor restarts the operation.

11. The processor for an endoscope according to claim 1, wherein the processor receives a reference image.

12. The processor for an endoscope according to claim 1, wherein the processor automatically controls the endoscope so as to increase the similarity in a case where it is determined that the similarity between the endoscope image acquired by the image sensor and a reference image is high.

13. The processor for an endoscope according to claim 12, wherein in a case where it is determined that the similarity between the endoscope image acquired by the image sensor while the processor controls the endoscope and the reference image has decreased, an operation of the automatic control by the processor is stopped.

14. The processor for an endoscope according to claim 12, wherein the processor outputs a notification in a case where the processor automatically controls the endoscope.

15. A training device comprising:
an image sensor that acquires an endoscope image;
a processor that records the endoscope image acquired by the image sensor in a case where the similarity between the endoscope image acquired by the image sensor and a reference image is higher than a predetermined threshold value, wherein the processor records the similarity between the endoscope image recorded by the processor and the reference image; and
a display that displays an evaluation of a manipulation based on the similarity recorded by the processor, wherein
the processor outputs a guide for increasing the similarity between the endoscope image acquired by the image sensor and the reference image associated with a region to be photographed with the guide superimposed on the endoscope image.

16. An information processing method for causing a computer to execute the following:
acquiring an endoscope image;
inputting the acquired endoscope image to a first learning model that outputs a target region corresponding to a predetermined region to be photographed when the endoscope image is input, and acquiring the target region;
displaying the acquired endoscope image and an index indicating the acquired target region with the acquired endoscope image and the index superimposed with each other;
outputting with the first learning model a plurality of target regions corresponding to a plurality of respective regions to be photographed when the endoscope image is input; and
displaying the endoscope image and an index indicating each of the plurality of target regions with the endoscope image and the index superimposed with each other.

17. A training method comprising:
acquiring an endoscope image;
recording the endoscope image in a case where the similarity between the acquired endoscope image and a reference image is higher than a predetermined threshold value;
recording the similarity between the recorded endoscope image and the reference image;
displaying an evaluation of a manipulation based on the recorded similarity; and
outputting a guide for increasing the similarity between the endoscope image acquired by the image sensor and the reference image associated with a region to be photographed with the guide superimposed on the endoscope image.

18. A non-transitory computer-readable medium containing a program for causing a computer to execute the following:
acquiring an endoscope image;
inputting the acquired endoscope image to a first learning model that outputs a target region corresponding to a predetermined region to be photographed when the endoscope image is input, and acquiring the target region;
displaying with a display the acquired endoscope image and an index indicating the acquired target region with the acquired endoscope image and the index superimposed with each other; and
outputting a notification when the display displays only an index corresponding to a reference image that does not conform to a predetermined observation sequence.

19. A non-transitory computer-readable medium containing a program for causing a computer to execute the following:
acquiring an endoscope image;
recording the endoscope image in a case where the similarity between the acquired endoscope image and a reference image is higher than a predetermined threshold value;
recording the similarity between the recorded endoscope image and the reference image;
displaying an evaluation of a manipulation based on the recorded similarity; and
outputting a guide for increasing the similarity between the endoscope image acquired by the image sensor and the reference image associated with a region to be photographed with the guide superimposed on the endoscope image.

* * * * *